United States Patent [19]
Widlanski

[11] Patent Number: 6,117,988
[45] Date of Patent: *Sep. 12, 2000

[54] NUCLEOTIDES AND OLIGONUCLEOTIDES PREPARABLE THEREFROM

[75] Inventor: Theodore S. Widlanski, Bloomington, Ind.

[73] Assignee: Advanced Research & Technology Institute, Bloomington, Ind.

[*] Notice: This patent issued on a continued prosecution application filed under 37 CFR 1.53(d), and is subject to the twenty year patent term provisions of 35 U.S.C. 154(a)(2).

[21] Appl. No.: 08/792,346

[22] Filed: Jan. 31, 1997

Related U.S. Application Data

[63] Continuation of application No. 08/792,346, Jan. 31, 1997.

[51] Int. Cl.[7] .................................................. C07H 19/00
[52] U.S. Cl. .................. 536/22.1; 536/23.1; 536/24.5; 536/25.3; 536/25.6; 536/27.6; 536/27.81; 536/28.5; 536/28.54; 536/115; 536/118
[58] Field of Search .............................. 536/22.1, 23.1, 536/24.5, 25.3, 25.6, 27.6, 27.81, 28.5, 28.54, 115, 118

[56] References Cited

U.S. PATENT DOCUMENTS

| | | | |
|---|---|---|---|
| 5,470,967 | 11/1995 | Huie et al. | 536/24.3 |
| 5,536,823 | 7/1996 | Widlanski | 536/27.6 |

OTHER PUBLICATIONS

Glemarec et al., Tetrahedron, vol. 49, No. 11, pp. 2287–2298 (1993).

Huie et al, j. Org Chem., vol. 57, pp. 4569–4570 (1992).

K.A. Perrin, J. Huang, E.B. McElroy, K.P. Iams, T.S. Widlanski, "Defining The Interactions Between DNA And The Exonuclease Domain Of DNA Polymerases", *J. Am. Soc.*, vol. 116, No. 16, pp. 7427–7428 (1994).

J. Huang, E.B. McElroy, T.S. Widlanski, "Synthesis Of Sulfonate–Linked DNA", *J. Organic Chem.*, vol. 59, No. 13, pp. 3520–3521 (1994).

E.B. McElroy, R. Bandaru, J. Huang, T.S. Widlanski, "Synthesis And Physical Properties Of Sulfonamide–Containing Oligonucleotides", *Biorganic & Medicinal Chemistry Letters*, vol. 4, No. 3, pp. 1071–1076 (1994).

Mirabelli et al., Anti Cancer Drug Design, vol. 6, pp. 647–661 (1991).

Uhlmann et al., Chemical Reviews, vol. 90, No. 4, pp. 544–584, (1990).

Musicki et al., Tetrahedron Letters, vol. 32, No. 10, pp. 1267–1270 (1991).

Reynolds et al., J. Org. Chem, vol. 57, No. 11, pp. 2983–2985 (1992).

*Primary Examiner*—James O. Wilson
*Attorney, Agent, or Firm*—Woodard, Emhardt, Naughton, Moriarty & McNett

[57] ABSTRACT

Analogues of RNA and DNA compounds contain a neutral, stereoregular linking group based on replacement of the phosphoryl with a sulfonyl group. Precursors to the analogues are also described, as are methods for preparing the precursors and analogues.

16 Claims, No Drawings

NUCLEOTIDES AND OLIGONUCLEOTIDES PREPARABLE THEREFROM

REFERENCE TO RELATED APPLICATIONS

This application is a continued prosecution application of U.S. application Ser. No. 08/792,346, filed Jan. 31, 1997.

BACKGROUND

Synthetic antisense oligonucleotides have shown great promise as agents for the selective modulation of gene expression in tissue culture. Antisense oligodeoxynucleotides, modified oligodeoxynucleotides such as phosphoramidate, phosphorthioate, and methylphosphonate oligodeoxynucleotides as well as 2'-O-methyl phosphorothioate oligonucleotides have also shown substantial inhibition of human immunodeficiency virus (HIV). Although the mode of action of antisense oligomers may be complex, especially for phosphorothioates, charged deoxyoligonucleotides are generally thought to express their antiviral activity by specifically binding to mRNA or viral genomic RNA thereby promoting cleavage of the hybrid by a viral or cellular ribonuclease H. Duplexes of modified DNA (such as methyl phosphonates) with mRNA do not form substrates for ribonuclease H, and their antiviral activity probably results from translation inhibition.

Some of the limiting factors that affect the efficacy of previous oligonucleotides as potential antisense agents are: (i) lack of nuclease resistance, (ii) insufficient chemical stability, (iii) poor membrane permeability and therefore low rates of cellular absorption, (iv) low affinity for complementary RNA, (or double stranded DNA in the case of triple helix formation) and (v) toxicity/lack of selectivity. As such there exists a continuing need for new oligonucleotides and precursors thereto, and to processes for their preparation. The present invention addresses these needs.

SUMMARY OF THE INVENTION

The present invention provides oligonucleotides containing a neutral, stereoregular linking group based on replacement of the phosphoryl group with a sulfonyl group.

Accordingly, one preferred embodiment of the invention provides an RNA or DNA analogue oligomer having a repeating unit of the general formula:

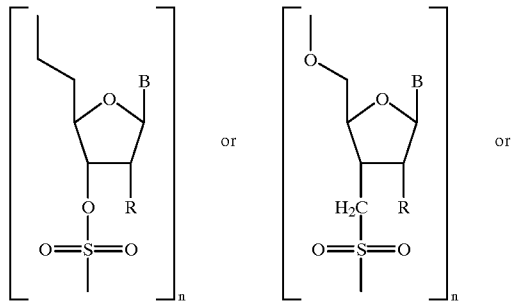

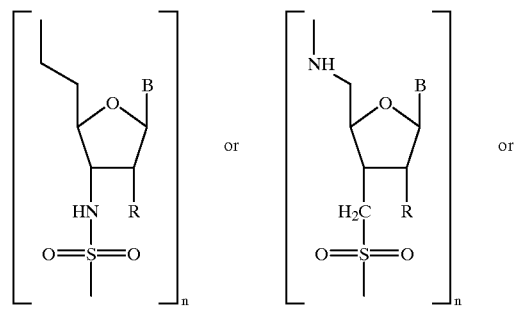

wherein n is an integer greater than or equal to 1, R=—H or protected or unprotected hydroxyl, and B is a protected or unprotected purine or pyrimidine base.

Another preferred embodiment of the invention provides a nucleoside monomer having the general formula:

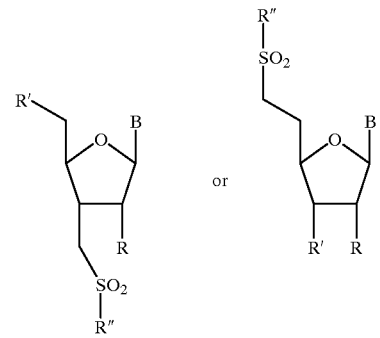

wherein R=—H or protected or unprotected hydroxyl; B=a protected or unprotected base selected from the group thymine, cytidine, adenine, and guanine; R'=protected or unprotected hydroxyl or amino; and R"=Cl, Br or a group of the formula —O—R'" wherein R'" is alkyl, generally $C_1$ to $C_{10}$ alkyl, and especially lower alkyl (i.e. $C_1$ to $C_5$ alkyl).

Additional preferred embodiments of the present invention relate to methods for preparing the above-noted oligomers and their monomeric precursors, for example involving glycosidation, Horner-Emmons and/or sulfinate chemistries as discussed below.

In accordance with one aspect of the invention, neutral DNA and RNA analogue oligomers ("oligos") are provided which may be used as antisense agents that have high chemical and biological stability, and do not contain chiral centers in the internucleosidic linkage. The use of sulfonate or sulfonamide analogues of DNA or RNA addresses difficulties described for other neutral DNA analogues such as methyl phosphonates or triesters. Sulfonyl analogues of DNA or RNA should, for the most part, enjoy very good chemical stability, since the sulfonyl group is highly resistant to cleavage at sulfur. In addition, the small structural variations that exist among the applicant's compounds allow for the control and assessment of subtle structural effects on double helix formation. Also, a direct comparison between the efficacy of modified RNAs and DNAs that are structurally similar (with respect to the modified backbone) is potentiated by the invention, both with regard to helix forming capacity and as antisense inhibitors of gene expression. In addition, incorporation of these sulfonyl derivatives at either end of an oligomer containing a central, short, unmodified region of normal DNA may generate an oligomer that can stimulate RNAse H activity but which will still be completely resistant to exonucleases and somewhat resistant to endonucleases. Thus, the applicant's invention provides compositions and methods that are vitally important to the study of DNA and RNA in a manner facilitating the development of new therapies and understandings, and may also find use in anitisense and other therapies.

Additional embodiments, features and advantages of the invention will be apparent from the following description.

DESCRIPTION OF THE PREFERRED EMBODIMENT

For the purpose of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

The applicant has developed several routes to precursors for the synthesis of oligonucleotides of the invention. Briefly, these routes involve mesylate anion chemistry, glycosidation chemistry, and Horner-Emmons chemistry. Additionally, sulfonate activation chemistry has been developed, which provides the ability to effectively couple monomers to form the inventive oligonucleotides. Each of these and other aspects of the present invention are more particularly described below.

The following abbreviations are used herein: Bn=benzyl; TBS=the tribenzylsilyl radical; TMS=the trimethylsilyl radical; Bz=benzoyl; Ph=the phenyl radical; DMTr=the 4,41-Dimethoxytrityl radical; FMOC=the 9-Fluorenyl-methoxycarbonyl radical; DBU=1,8-Diazabicyclo[5.4.0]undec-7-ene; THP=the tetrahydropyran radical; MMTr=the p-monomethoxytrityl radical; $C^{Bz}=N^4$ Benzoylcytidine; $A^{Bz}=N^6$Benzoyladenine; $G^{N-9Ac}=N^9$ Acetylguanine; Me=the methyl radical; Et=the ethyl radical; A=the propyl radical; Bu=the butyl radical; TFA=trifluoroacetic acid; Py=pyridine; DMAP=dimethylaminopyridine; RT=room temperature; HMDS=hexamethyldisilazane; Tf=triflate; and THF=tetrahydrofuran.

Mesylate Anion Chemistry

The mesylate anion chemistry as applied to the preparation of the sulfonate analogue of UMP is described by Muskicki, B., and Widlanski, T. S., in *J. Org Chem.*, 1990, Vol. 55, pp. 4231–33. In addition to the sulfonate analogue of UMP, the applicant has discovered that this method can successfully be used to synthesize the sulfonate analogue of TMP. 5-Deoxy-5-iodo-thymidine (available in about 80% yield from thymidine by reaction with triphenyl phosphine/I in pyridine) was protected as its 3'-O-TBS ether as shown in Scheme I below. Reaction of this iodide with the anion of an alkyl mesylate, e.g. isopropyl mesylate, gives the sulfonate ester in about 70% isolated yield. The ester may be deblocked, for instance with tetra-n-butyl ammonium iodide.

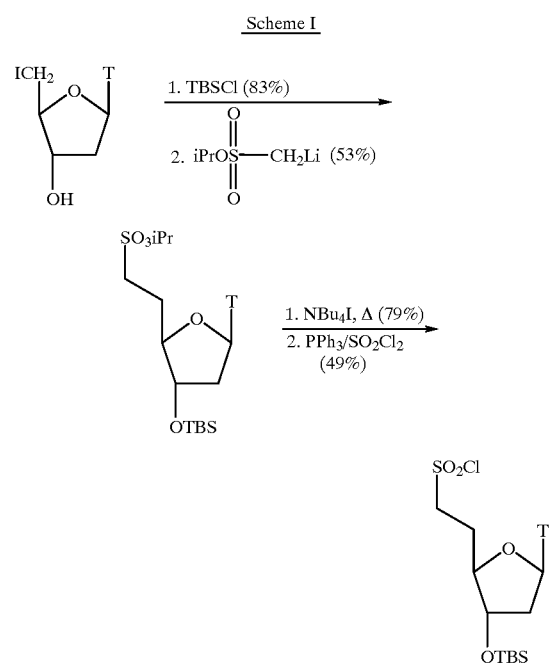

Scheme I

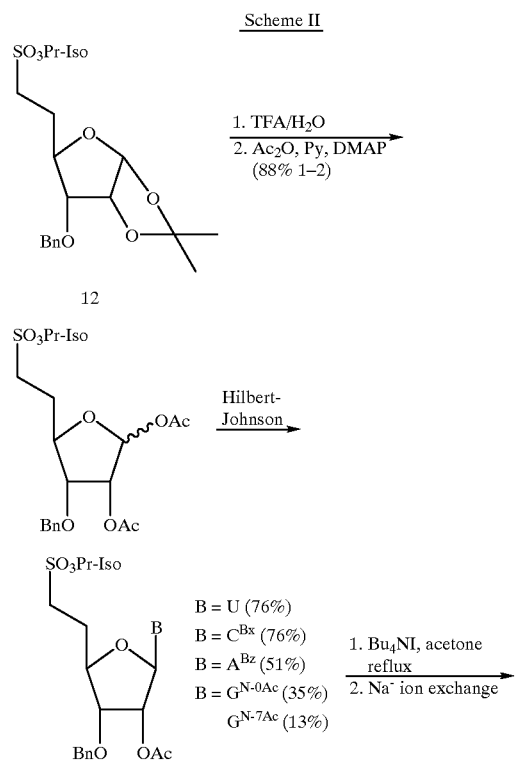

Glycosidation: The glycosidation chemistry which is used to synthesized nucloside sulfonates is analogous to methods used for synthesis of nucleosides from ribose (modifications of the Hilbert-Johnson reaction). All of the RNA monomer analogues described above were synthesized by this method as set forth in Scheme II below.

Scheme II

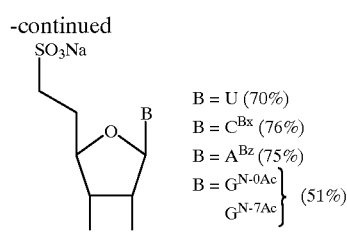

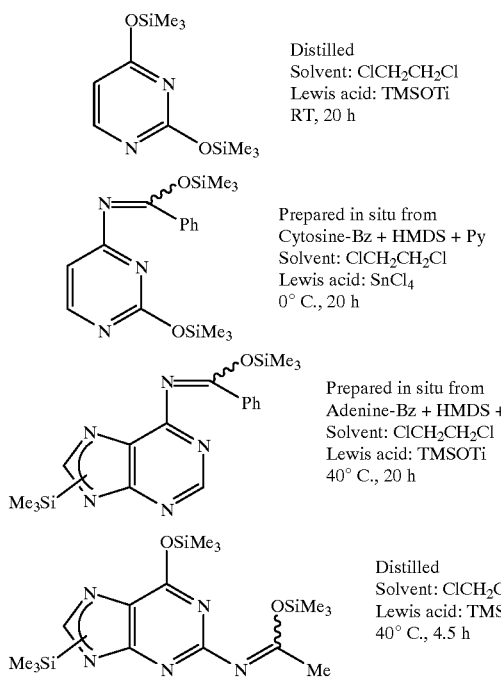

Thus, the protected ribose 5-sulfonate (12) was converted to a mixture of 1,2 diacetates and subjected to Hilbert-Johnson glycosidation (Niedballa, U.; Vorbruggen, H. *J. Org. Chem.*, 1974, Vol. 39, p. 3654: Vorbruggen, J.; Krolikiewicz, K; Bennua, B., *Chem. Ber.*, 1981, Vol. 114, p. 1234: Garner, P.; Ramakanth, S., *J. Org. Chem.*, 1988, Vol. 53, p. 1294) under the conditions shown. In all cases reasonable yields of the sulfonate nucleosides were obtained. Using preparative TLC it was possible to separate the mixture of regioisomers resulting from glycosidation using silyated gaunosine acetate as the base. However, for the purpose of demonstrating the deprotection, a mixture of the two isomers was used. Glycosidation with silylated uracil and cytosine derivatives was particularly effective. Cleavage of the isopropyl ester was effected by treatment of the sulfonates with Bu $_4$NI in boiling acetone. The salts were then purified by flash chromatography using mixtures of EtOAc/EtOH/Et $_3$N as eluent.

Interestingly, the Hilbert-Johnson on glycosidation of carbohydrate sulfonates can be used with disaccharide sulfonates to give dinucleosides as shown in Scheme III. The primary acetonide of the disaccharide sulfonate 6 (see Scheme XXI below) was selectively hydrolyzed, followed by periodate cleavage, borohydride reduction of the resulting aldehyde and finally protection of the 5-OH as a benzoate ester. Removal of the two remaining acetonides of the disaccharide followed by conversion to a mixture of tetraacetates is straightforward. The Hilbert-Johnson glycosidation of this disaccharide with silylated cytosine benzoate gave the dinucleotide in 76% yield. Deprotection of the ester groups by treatment with 10% methanolic ammonia (50° C., 12 hours) was virtually quantitative. Importantly, no evidence of 3'-cyclonucleoside formation was observed under these conditions. In fact, no cleavage of the sulfonate linkage occurred even after boiling of the dinucleotide with saturated methanolic ammonia for 24-hours. This evidences that oligomers linked via a 3'-sulfonate group enjoy high chemical stability.

Scheme III

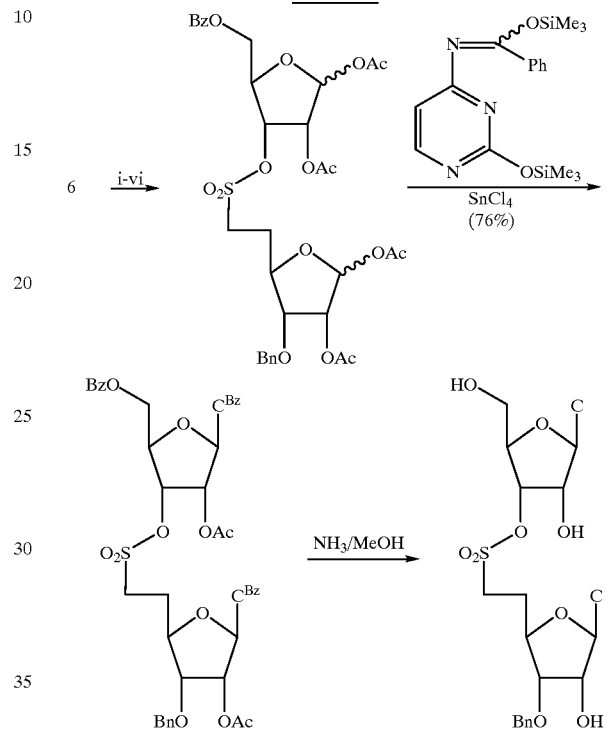

i, THF/MeOH/H$_2$O/HCl (76%); II, NaIO$_4$; III,NaBH$_4$; iv, BzCl (87% ii-Iv); V, TFA/H$_2$O; vi, Ac$_2$O/Py (89% v-vi).

Further as to the glycosidation chemistry, although syntheses that proceed through ribose are longer than those that start with a nucleoside, the ribose methods offer greater flexibility to incorporate modified bases which enhance the stability of double or triple stranded helices. Methodology which allows for the substitution of altered bases for normal ones provides a further dimension to the design of antisense agents which may enhance heteroduplex stability with targeted mRNAs. This benefits probes targeted toward translation arrest and similar strategies for antisense activity (in addition to the stimulation of RNAse H activity). In this context it is important to note that it is likely that sulfonyl-containing helices are metabolically inactive. Accordingly, using sulfonyl-containing helices, there will be more latitude to incorporate oligonucleotide bases which, if incorporated into metabolizable DNA or RNA, might by cytotoxic. It is preferred to synthesize primarily the primidine-containing sulfonyl-linked RNA by glycosidation chemistry, since glycosidation chemistry for DNA yields mixtures of anomers. However, for some purposes, e.g. for evaluating helix-forming tendencies of oligos, it is practical to initiate the syntheses of sulfonyl-linked RNA by examining glycosidation chemistry, especially for the 3'-O and 3'-N-sulfonyl derivatives, since all the nucleosides may be synthesized from a common precursor. This simplifies work such as base modifications.

Horner-Emmons Chemistry:

The applicant has discovered that Horner-Emmons chemistry can be successfully used to synthesize the nucleoside sulfonates (see Scheme IV, in which of course Et may be replaced by any organic group conventionally employed in Horner-Emmons reactions, for example other alkyl groups such as lower alkyls, and A may be replaced by other nucleotides, e.g. C, G, T or U). In addition to glycosidation chemistry, this methodology forms a primary mode by which all the nucleoside sulfonates, with the exception of thymidine and uridine, are preferably synthesized (uridine and thymidine sulfonates are more easily synthesized via the sulfonate anion chemistry previously described.) The Horner-Emmons chemistry involves the reaction of sulfonyl-stabilized α-phosphonate anions (Carretero, J. C.; Denillequand, M.; Ghosez, L., *Tetrahedron*, 1987, Vol. 43, p. 5125) with a protected adenosine aldeliyde (1) (Ranganathan, R. S.; Jones, G. H.; Moffatt, J. G., *J. Org. Chem.*, 1974, Vol. 39, 290) (eq 1). This reaction gave the α,β-unsaturated sulfonate ester (2). Reduction of the double bond with NaBH$_4$ followed by hydrolysis of the acetonide and ammonolysis of the sulfonate ester and N-benzoyl protecting groups gave adenosine 5'-sulfonate (41% overall yield based on 1).

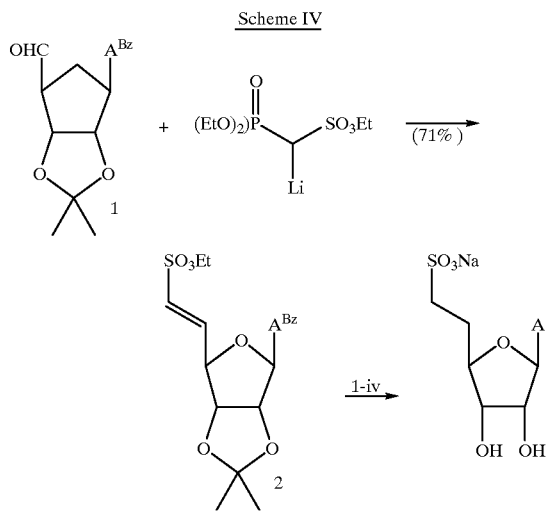

Scheme IV i, NaBH$_4$, (70%); II, TFA/H$_2$O; III, NH$_3$/MeOH; iv, Na$^+$ Ion exchange, (83%) ii-Iv).

This chemistry has also been used to couple nucleosides together to give a sulfonate linkage. In applicant's work thus far, coupling yields with nucleoside 5' aldehydes have been quite good. Even coupling reactions between two nucleosides give goods yields of the E-α,β-unsaturated sulfonate. Yields typically range between 70–90%, with 80–90% usually the norm. Even with carbohydrate ketones, the yields are quite good, giving a mixture of the two possible olefins. This result is in direct contradiction to literature statements that Horner-Emmons reactions of this type give poor yields with ketones. This probably reflects the fact that the carbohydrate ketones are more reactive than these ketones previously studied. The Horner-Emmons reactions yield α,β-unsaturated sulfonates which may be reduced by a variety of reagents that effect conjugate reduction, such as NaBH$_4$, copper hydride hexamer, and LiBH$_4$. LiBH$_4$ is generally useful for less reactive substrates such as the trisubstituted α,β-unsaturated sulfonates that result from the Horner-Emmons reaction with ketones.

Sulfonate Activation

The applicant has developed a method for the synthesis of sulfonyl halides under very mild conditions which is useful for the activation of nucleoside sulfonates. By treating sulfonate salts with PPh$_3$ and a suitable halogen donor, e.g. SO$_2$Cl$_2$ in an inert solvent such as a haloalkane, e.g. methylene chloride, very good isolated yields of sulfonyl chlorides, often greater than 90%, are obtained. Unlike other known methods for the synthesis of sulfonyl chlorides, the inventive method is tolerant of very sensitive functionality. Thymidine sulfonate reacts rapidly with the PPh$_3$/SO$_2$Cl$_2$ reagent, even at −78° C. to give the sulfonyl chloride, which was isolated in 60% yield. Although the yield of this reaction is lower than that obtained with carbohydrate sulfonates, it is expected that the reaction is just as good. The relatively low yield of this particular reaction is likely related to the instability of the sulfonyl chloride on silica (in contrast to many of the other sulfonyl chlorides synthesized). Once purified, the sulfonyl chloride is a stable solid which can be crystalized fairly easily. Modifying isolation and purification techniques should allow a substantial improvement in yield for this reaction. Other nucleosides are also suitable as substrates for this reaction.

The synthesis of 3'-O-sulfonates proceeds via coupling to a 3'OH group, which is secondary, rather than coupling to a primary 5'OH group (as in standard oligonucleotide syntheses). The applicant has demonstrated this general approach in several ways. First, by the coupling of the thymidine sulfonyl chloride to simple alcohols, such as isopropanol. The reaction is very clean, and proceeds in virtually quantitative yield. NMR of the crude reaction mixture shows complete disappearance of the starting material and its replacement by the known isopropyl sulfonate ester. No byproducts were observed in this coupling. Second, by the coupling of a model sulfonyl chloride (derived from ribose) to the very hindered secondary hydroxyl group of diacetone allose. The isolated yield of this reaction was always greater than 95%. Moreover, the applicant has synthesized an octomer of sulfonate-linked thymidine using this methodology. In short, the applicant's work has evidenced that these coupling reactions proceed in excellent yield, regardless of whether the alcohol is secondary or primary.

Sulfinate Chemistry

Another focus of the applicant's work is on the use of trialkylsilyl alkyl sulfonate, e.g. TMS ethyl sulfinate, chemistry (Scheme V), which applicant has also used in the synthesis of steroid sulfonates (see discussion below). This reaction is a practical replacement for the Strecker reaction (the reaction between bisulfite and an alkyl halide) which has several added benefits. The product sulfone may be deprotected under very mild conditions to give a sulfinate. Since sulfinates are easily oxidized to sulfonyl chlorides, the method provides an alternative route to activated sulfonates not previously available. This chemistry is a nice complement to the sulfonate anion and sulfonate Horner-Emmons chemistry in that a TMS sulfone group can be used in a manner analogous to a sulfonate ester, but, with the following advantages: (1) The sulfone anion is much more stable than the sulfonate anion, and could therefore be used with less reactive substrates; (2) The TMS ethyl sulfone group would be compatible with more chemistry than the sulfonate ester group, particularly with regard to nucleophiles, which react with the sulfonate ester; (3) Deprotection can be effected with fluoride ion under very mild conditions; (4) Oxidation of the sulfinate to the acid chloride is an exceptionally mild reaction.

Scheme V

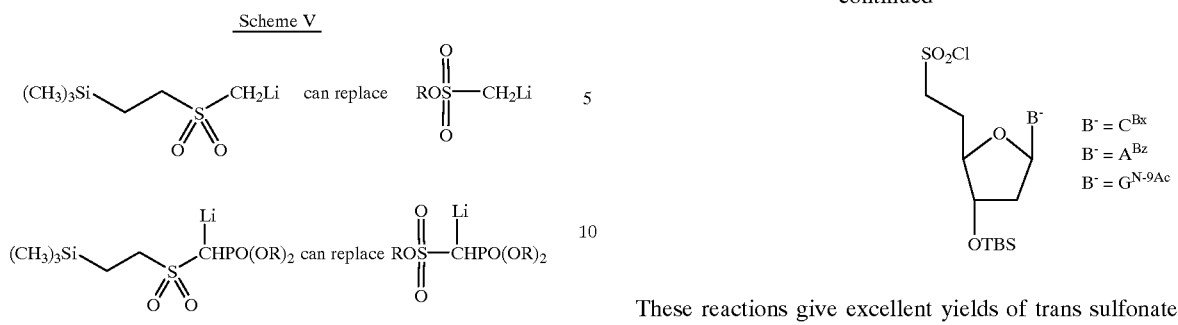

To promote a further understanding and appreciation of the invention and its preferred embodiments and advantages, the following specific Examples are provided. It will be understood, however, that these examples are illustrative, and not limiting, in nature.

EXAMPLES

Synthesis of Monomer 1

A route to the monomers for synthesis of 3'-O-sulfonates is shown in Scheme VI below, in which R can be any organic group conventionally employed in Horner-Emmons chemistry, especially lower alkyl such as ethyl. The activated thymidine analogue was prepared as described above, by the mesylate anion chemistry route. The other three bases can be synthesized using Horner-Emmons chemistry exactly analogous to that used to synthesize the corresponding RNA analogues (see Syntheses below). The aldehyde is prepared by bis silylation of the nucleoside, followed by selective hydrolysis of the primary TBS ether. (The small amounts of doubly deprotected materials generated in this reaction may be recycled.) The primary alcohol is converted to the aldehyde by a Swern oxidation. The aldehyde, which is analogous to those used for RNA syntheses, is reacted with a phosphonate-stabilized a-sulfonate anion in a Wadsworth-Horner-Eimmons type of reaction.

Scheme VI

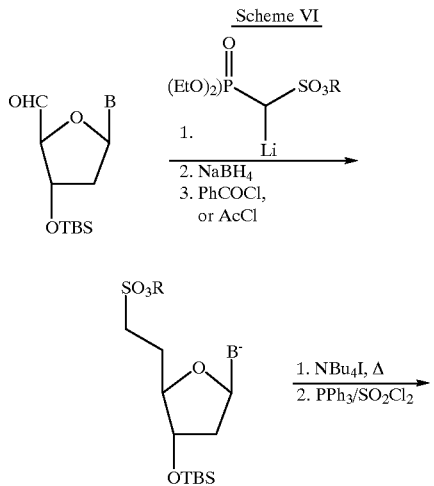

These reactions give excellent yields of trans sulfonates with nucleoside aldelhydes of the ribose series. The base may be protected at the beginning of the synthesis, or after introduction of the sulfonyl group. After reduction of the double bond and protection of the base by acylation, (should this pathway be used rather than protection of the base at the outset) the sulfonate ester is cleaved by treatment with iodide, and the resulting salt is activated with $PPh_3/SO_2Cl_2$. If deprotection of the oligoiner (deacylation of the bases and cleavage of the oligomer from the resin) is performed under conditions that cleave the 3'-O-sulfonate ester, rapid deprotecting a-alkoxy esters can be used to protect the bases.

Synthesis of Monomer 2

The 3'-O-sulfonate monomers are synthesized by deoxygenation of the corresponding ribo derivatives shown in Scheme VII below. The need for proceeding via the ribo compound is dictated by the instability of 3'keto derivatives of deoxynucleosides, which have a strong tendency to undergo elimination. The synthesis of the starting ribo sulfonates is described under Synthesis of (6). After deoxygenation, the sulfonate ester may be deprotected and activated as previously described for monomer (1).

Scheme VII

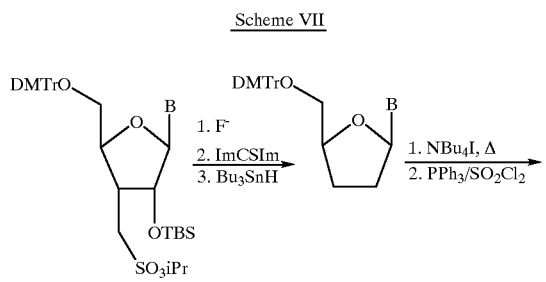

At this point, it is germane-to address the stability of the 5' sulfonate esters. Unlike secondary carbohydrate sulfonates, which are relatively poor electrophiles, primary sulfonates, such as the 5' sulfonate esters described here, are much better electrophiles.

To assess stability of the 5'-O-sulfonates various ribo and deoxyribo 5'mesylate nucleosides were synthesized. For both steric and electronic reasons the mesylates are exepected to be even more reactive than the 5'O-sulfonate-linked oligos. These compounds are therefore good models for the stability of the 5'-O-sulfonates. Testing has revealed that 5'-O-mesylates react only relatively slowly with 90% MeOH/NH$_4$OH at 30° C. Further, the mesylates appear very stable in 1:1 MeOH/triethylamine, and completely stable over several hours to 1:1 MeOH/diisopropyl ethylamine. (No decomposition at all was noted under these conditions.) These types of conditions should be sufficient for the deblocking of rapid deprotecting groups such as α-alkoxy esters. Indeed it may even be sufficient to use anhydrous MeOH/NH$_3$ in order to effect clear deprotection. Still further blocking strategies may be used if necessary. For example, Weinreb's group has reported the use of the TMS ethyl sulfonyl group as a protecting groups for amines. This protecting group can be removed by treatment with fluoride ion. The TMS ethyl sulfonyl group has been used to protect a variety of amines, even pyrroles. Since nucleoside amines are much better leaving groups than normal amines, this sulfonamide protecting group should be removable under very mild fluoride ion treatment. This protecting group strategy should provide the synthesis of 3'-O-sulfonates, since such a protecting group obviates the need for ammonolysis of the base protecting groups. Use of the nonbasic triethyl ammonium fluoride should ensure that conditions of silyl group cleavage do not become basic. While it is true that under certain conditions fluoride ion can behave as a fairly strong base, the usual reason fluoride ion cleavage of silyl ethers or amines is so basic is because there is no proton available to protonate the alkoxide or amide generated in the reaction. The presence of a proton on the ammonium group of trielhyl ammonium fluoride attenuates the basicity of the fluoride ion, and provides a proton source to protonate the leaving group. This gives rapid reactions under very mild conditions.

Synthesis of Monomer 3

The sulfonamides have the advantage over the sulfonates in that they are more stable, even under fairly extreme conditions. The 3'-N-sulfonyl derivatives are synthesized from the 3'azides as shown in Scheme VIII below. After introduction of the sulfonate group by sulfonate anion (for thyinidine) or Horner-Emmons chemistry, the azide is reduced, and protected as an FMOC carbamate. The sulfonate ester is deblocked, and activated as shown. Chain elongation steps consist of elimination of the FMOC group with DBU, followed by treatment with an activated monomer. Any unreacted amino groups are then capped by treatment with Ac$_2$O.

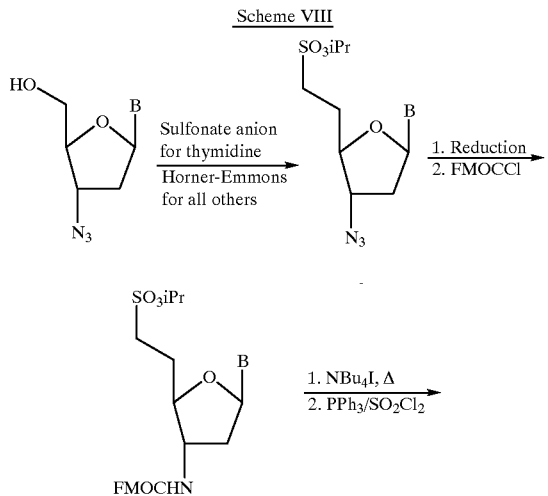

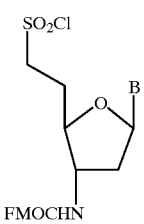

Synthesis of Monomer 4

The synthesis of this material proceeds via the previously described intermediate as shown in Scheme IX below. The 5' protecting group is removed and the 5'OH converted to the tosylate. Displacement with azide, followed by reduction provides the amine, which may be protected as an FMOC carbonate. The rest of the synthesis then parallels that described for the 5'-O-sulfonate, as shown. Chain elongation steps consist of elimination of the FMOC group with DBU, followed by treatment with an activated monomer. Any-unreacted amino groups are then capped by treatment with Ac$_2$O.

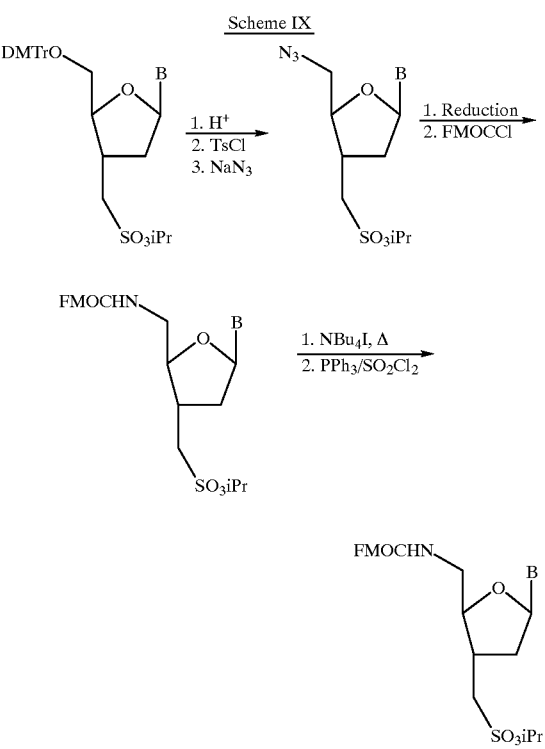

Synthesis of Monomer 5

The synthesis of oligoribonucleotides is more complex than the analogous deoxynucleotides because of the presence of the vicinal syn hydroxyl groups at the 2' and 3' positions. Protecting groups on the 2'OH must be amenable to removal under very mild conditions, but must also be compatible with protecting group and coupling chemistry characteristics of the overall synthesis. In addition, the protecting group at the 2' position must not be susceptible to vicinal migration. Under these circumstances, special ethers may be used which can be removed under mild conditions at the finish of the synthesis. Typical of such a strategy is the use of o-nitro benzyl ethers, which have been employed as 2'OH protecting groups. (These ethers may be removed by photolysis). Another favored approach is to use a sulfonate ester as a protecting group. Sulfonates do not undergo vicinal migration to syn OH groups, and can be put on the 2' position with some selectivity, although care must be taken to ensure that they do not undergo cyclonucleoside formation under basic conditions, and in their removal at the end of the synthesis.

These considerations may also be overcome by using a TMS ethylsulfonyl group as a protecting group for the 2'OH. Providing that the oligomer is not exposed to basic conditions, the sulfonyl group should be stable. At the end of the synthesis, prior to removing protecting groups from the bases, the oligomer is treated with triethyl ammonium fluoride to deblock the 2' position. If this protecting group is also used on the bases, one may effect a complete deblocking of the oligo in one very mild and efficient step.

The monomer synthesis set forth in Scheme X below avoids basic conditions, and provides a 3' protecting group that can be removed with great facility under conditions compatible with oligonucleotide synthesis. Chain elongation is accomplished by acidic hydrolysis of the THP group, followed by homologation, and then coupling.

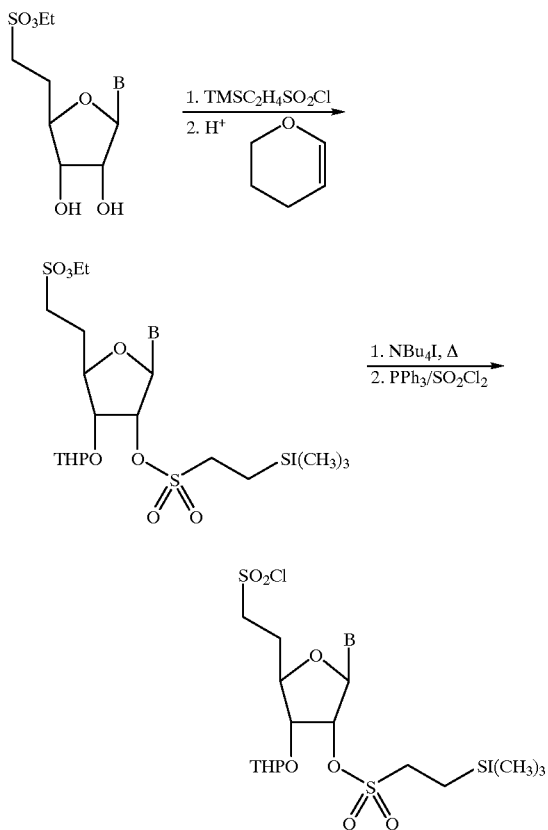

Sythesis of Monomer 6

Two alternative routes to the monomers necessary for the synthesis of 5'-O-sulfonyl-linked RNA are shown in Scheme XI below. The first method starts from material already reported (3 steps from diacetone glucose, 73% overall yield). Protecting group modifications can be used in order to accommodate the base lability of the 5'-O-sulfonate ester.

For instance, p-nitrobenzoates can be used instead of benzoates. This method has the advantage that all of the necessary nucleosides can be generated from a common precursor. The second method for the synthesis of these activated monomers has the advantage in that it is relatively short. Selective silylation of uridine followed by Swern oxidation and Horner-Emmons chemistry gives the unsaturated sulfonate. The 5' silyl group, which is now much less hindered than the 3' silyl group is selectively hydrolyzed. If selective hydrolysis is not possible, one can simply start with a DMTr ether at the 5' position. The olefin is then reduced by a directed hydride reduction with sodium triacetoxy borohydride. The 5' position is then protected and the sulfonate deblocked and activated as shown.

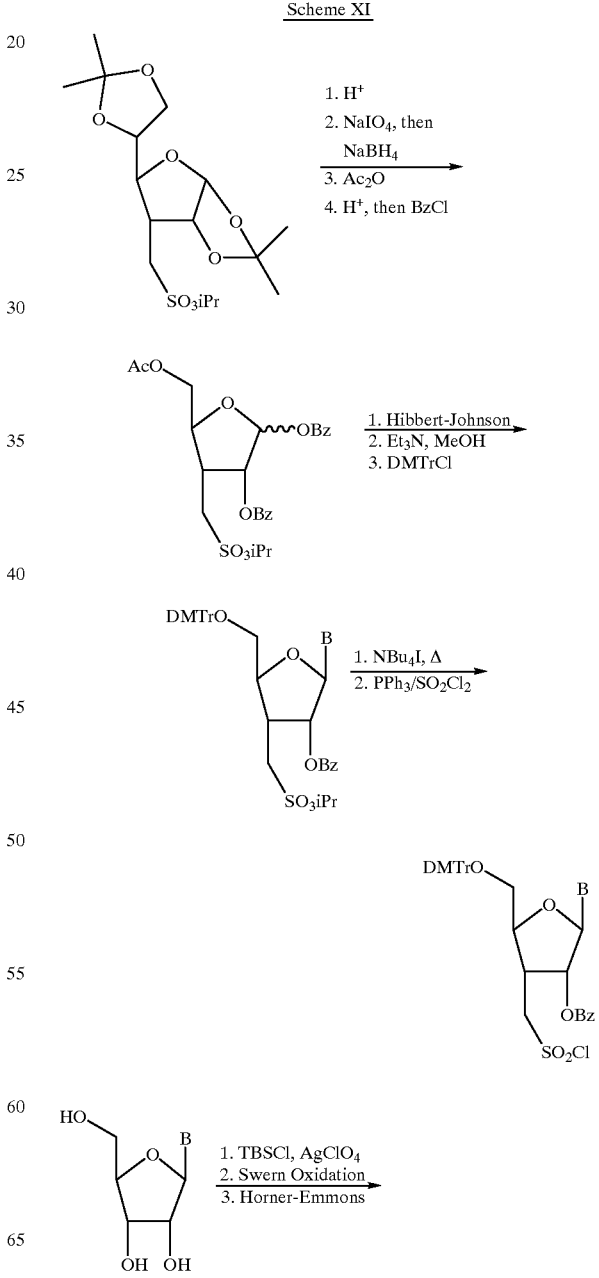

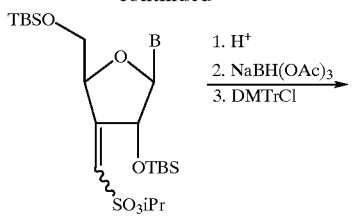

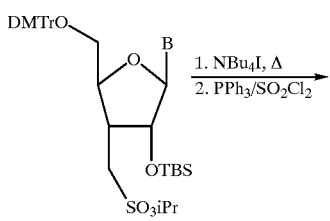

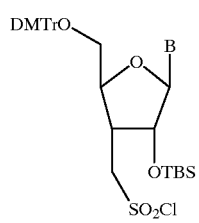

Synthesis of Monomer 7

A synthesis of 7 is diagrammed in Scheme XII below. The synthesis parallels that described for the deoxy analogue. The 2'OH is selectively silyated, and the 3'OH inverted via a Mitsunobu reaction. This center is activated as a triflate and displaced by azide. Reduction of the azide is followed by protection as an FMOC carbamate. Deblocking of the sulfonate and activation then complete the monomer synthesis.

Scheme XII

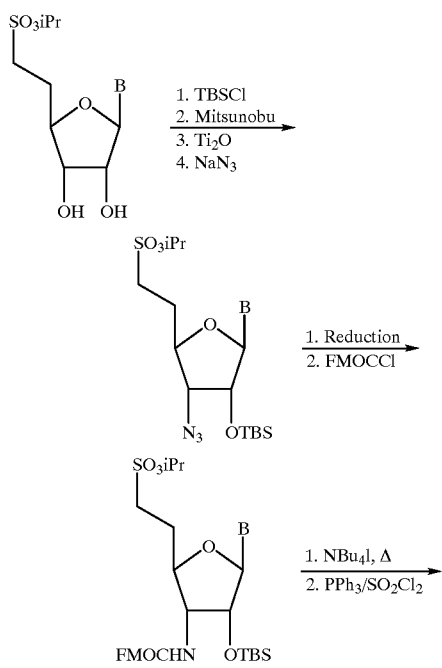

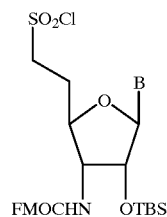

Synthesis of Monomer 8

A synthesis of the monomer for preparation of 5'-N-sulfonamides is shown below in Scheme XIII. The 5'OH is activated and displaced by azide, followed by reduction to the amine, and protection of the amine as an FMOC carbamate. The sulfonate is then deblocked and activated as shown.

Scheme XIII

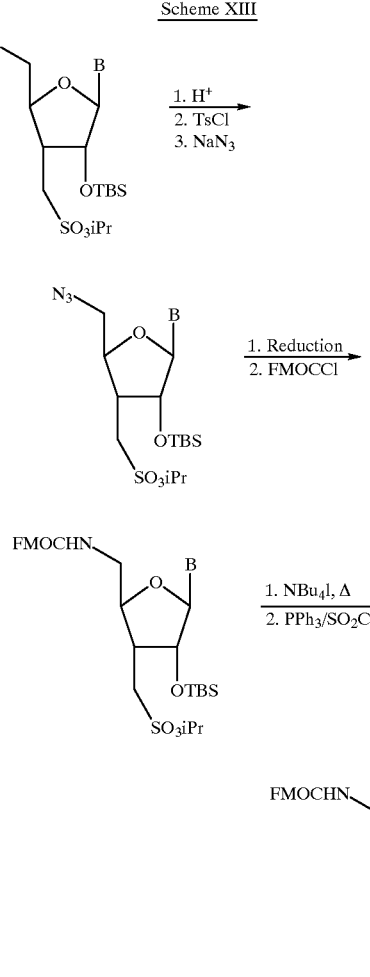

Synthesis of Oligonucleotides

Oligomers synthesized from the monomers and procedures above have the following formulas:

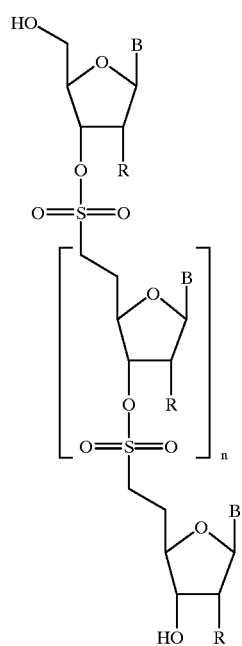
1 R = H:5 R = OH
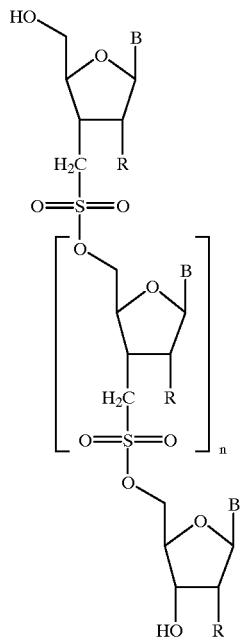
2 R = H:6 R = OH
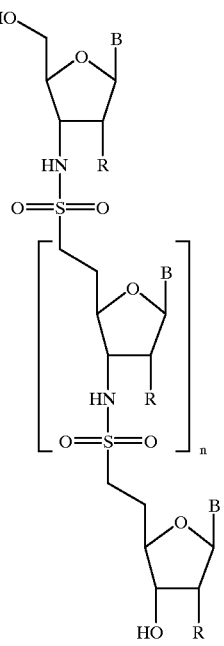
3 R = H:7 R = OH
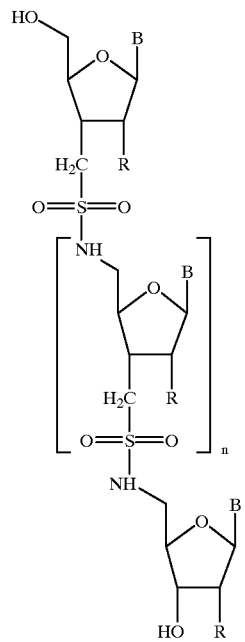
4 R = H:8 R = OH wherein n is an integer greater than or equal to 1, R=—H or protected or unprotected hydroxyl, and B is a protected or unprotected purine or pyrimidine base "n" will generally be in the range of 1 to about 200. B, of course, can vary within the oligomer (i.e. oligomers having 1, 2, 3, 4 or more different base types can be prepared). In one illustrative preparation, treatment of thymidine with PPh$_3$/I$_2$ in pyridine at 0° C. gave the 5'-iodide (Scheme XIV) which was not isolated, but silylated directly to give 2 (88%). Alkylation of 2 proceeded in good yield (68%) to give the desired sulfonate. The sulfonate ester was deblocked in quantitative yield with Bu$_4$NI to give the salt. The sulfonate salt was treated with PPh$_3$/SO$_2$Cl$_2$ to give the labile acid chloride in 63% yield after flash chromatography (37% overall yield from thymidine).

second round of coupling and deblocking to give a trimer could then be effected. Subsequent iterations were repeated to give an octamer. The coupling of the incoming acid chloride and the 3' OH of the growing chain is almost quantitative even on the very small scales used (typically between 10–20 mg of oligomer) with isolated yields consistently in the range of about 90%. The longer oligomers are more difficult to solubilize and while yields were somewhat reduced in later steps the coupling could be continued.

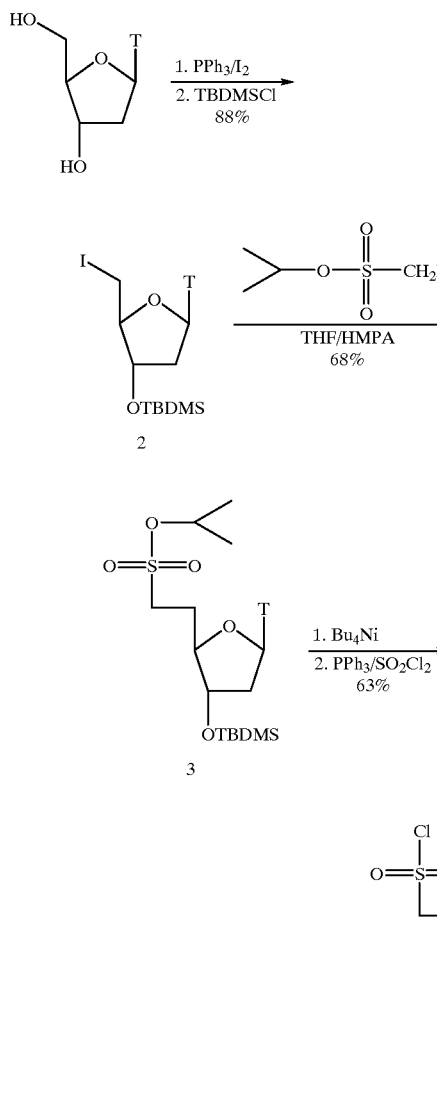

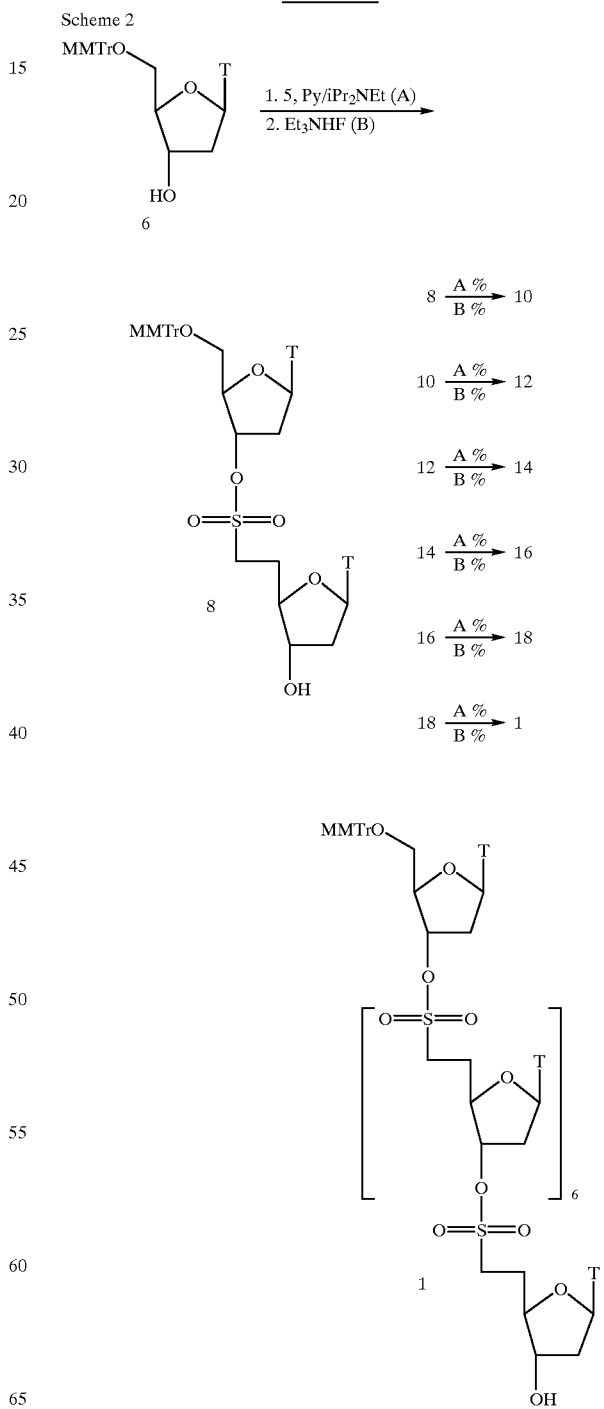

Treatment of the sulfonyl chloride 5 with pyridine and diisopropyl ethylamine in the presence of 5' MMTr thymidine gave the sulfonate-linked dimer in 94% isolated yield. The 3' end of the dinucleoside could be easily deblocked by treatment with an excess of triethylammonium hydrofluoride to give a 5' protected sulfonate-linked dinucleoside. A Applicant has also attached a sulfonate-linked dinucleoside to a solid support and used the charged support to synthesize DNA containing a 3' sulfonate-linked dinucleoside. In addition, a sulfonate-linked dinucleoside containing a 3' phosphoramidite has been used to synthesize DNA containing a sulfonate linkage at various points.

Synthesis of Chimeric Oligodeoxyribonucleotides

Two different classes of chimeric oligomers may be synthesized. The first type bears non-degradable sulfonyl-linked DNA at the 5' and 3' regions and has a central region of unmodified DNA which should provide a recognition element for RNAse H. Of this type of chimeric oligo there are two general types of constructs that may be synthesized, those that have 5'-O-sulfonate linkages and those that have 3'-O-sulfonate linkages.

Chimeric DNA with 5'-O-Sulfonates

The 5'-O-sulfonate-linked DNA is the easiest to adapt to chimeric synthesis since the directionality of the DNA synthesis is identical to that normally used for automated DNA synthesis. The chain will grow from the 3' end by iterative coupling to the 5'OH group via the activated sulfonyl chloride monomers previously described. When a sufficient length of sulfonates has been synthesized, the newly deprotected 5'OH group will be coupled to a phosphoramidite by standard DNA coupling methods. Phosphoramidites are added until a sufficient length of natural DNA has been assembled to give a recognition site for RNAse H. After detritylation of the last phosphate-linked residue, one may resume adding sulfonates by 5' coupling to the sulfonyl chloride monomers. The overall synthesis is set forth in Scheme XVI below. 5'-N-sulfonamides may also be adapted to this type of chimeric synthesis.

Since the 5'-O-sulfonates are somewhat base labile, the nucleoside bases are protected as rapid deprotecting amides (α-alkoxy acyl groups). Alternatively, the bases may be protected as TMS ethyl sulfonamides, as described earlier. The linking group can be rapid deprotecting as well. Oxalate esters have been shown to provide the requisite stability for DNA synthesis, but are removed under very mildly basic conditions. Thus deblocking may be accomplished by treatment with methanolic diisopropyl ethylamine, conditions applicant has shown do not affect 5'-O-mesylates.

Chimeric DNA with 3'-O-Sulfonates

The synthesis of chimeric DNA with 3'-O-sulfonates has a different directionality associated with it than that usually employed for DNA synthesis. There are two avenues to address this. First, the directionality of DNA synthesis may be reversed. Historically, some of the first oligonucleotide syntheses used this approach (the phosphodiester approach). However, given the very high reactivity of phosphoramidites, a 5' phosphoramidite will react reasonably well with a 3'OH group. (Indeed, the amidites are synthesized to begin with by coupling of the 3'OH to a bis-amidite.) The yield of this reaction may be lower than that realizable with a primary alcohol as a nucleophile, and the time required for coupling may be slightly longer, but the amidites should be easily synthesized and compatible with standard solid phase techniques. This strategy is shown in Scheme XVII below. Since the longest stretch of phosphodiester linkates incorporated will likely be six, (based on the probable length necessary for recognition by RNAse H) a 90% yield in the coupling reaction would translate to 53% yield for synthesis of the phosphorylated region of the DNA. It is expected that the yields of such coupling reactions will be much higher, but even such a modest coupling yield is quite acceptable. Deblocking of the oligo is accomplished by treatment with methanolic ammonia.

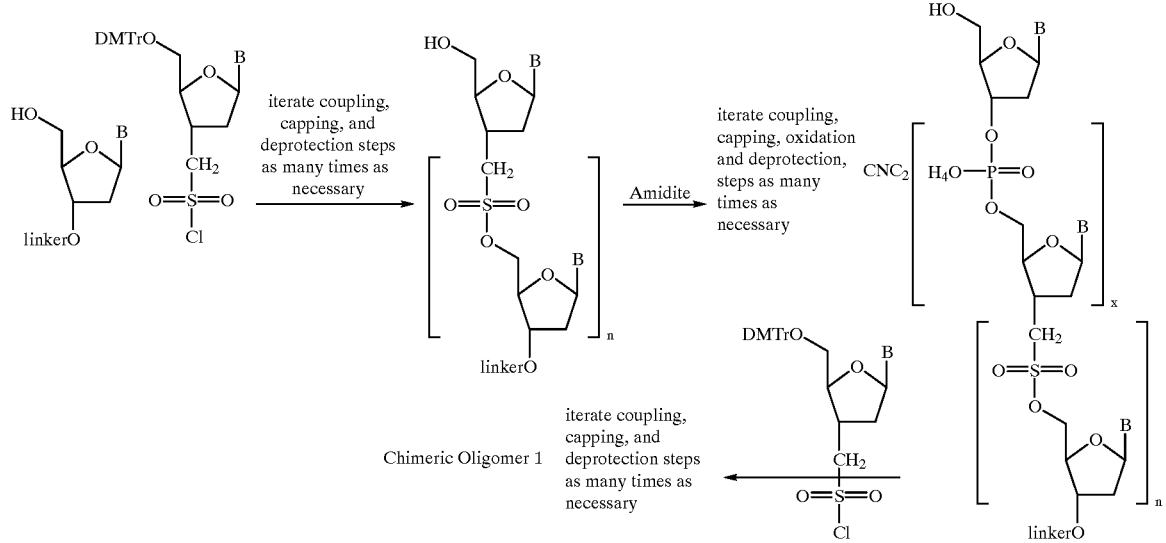

Scheme XVI

Scheme XVII
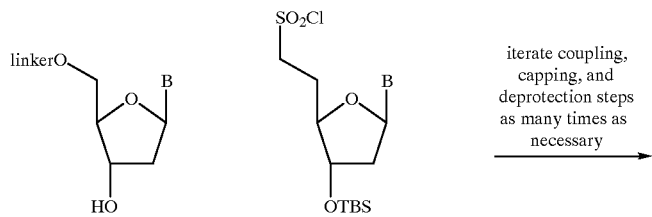
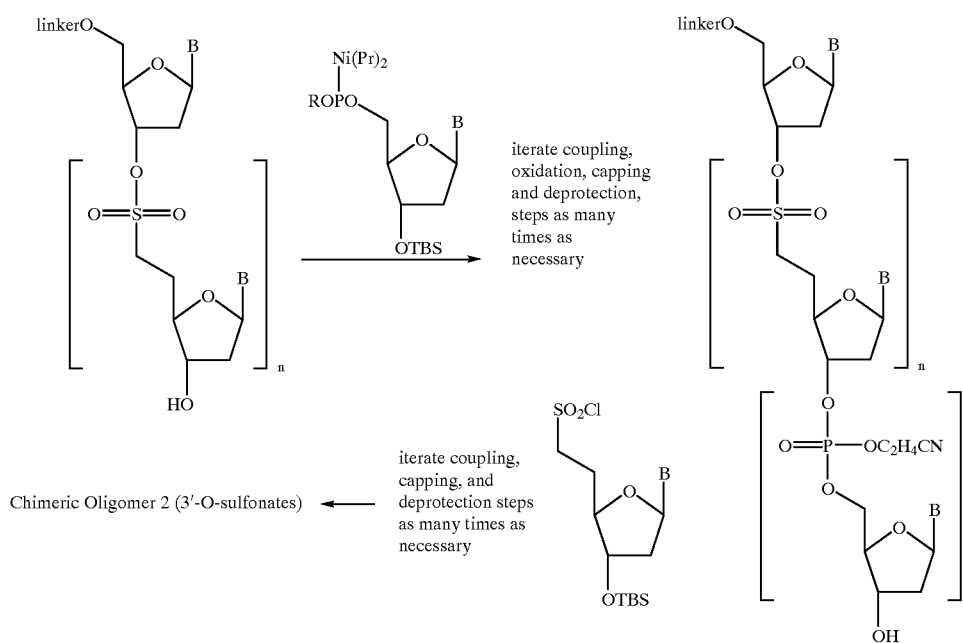
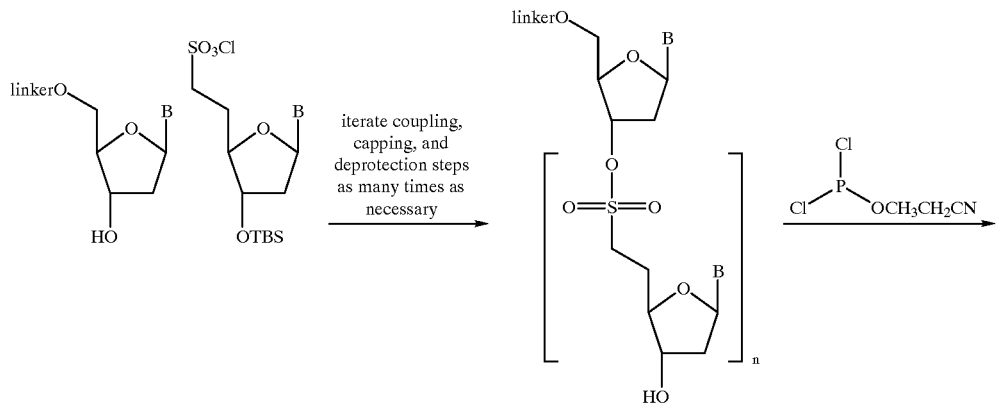

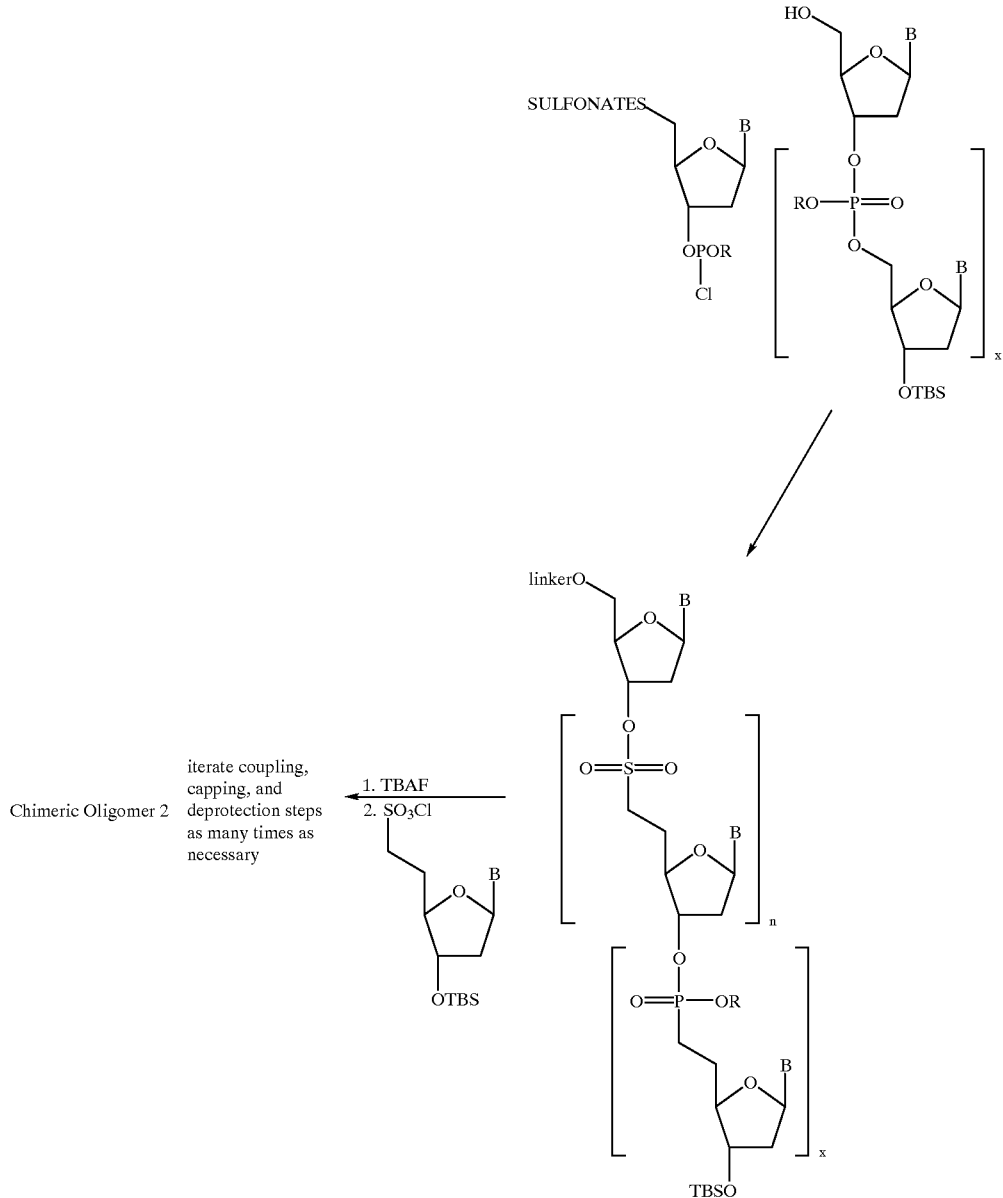

An alternative preparation is also set forth in Scheme XVII. This preparation involves the synthesis on-line of the 5'sulfonate region. The 3'OH is then activated by reaction with a phosphodichloridite (this type of activation was first introduced by Letsinger for rapid DNA synthesis), to give a 3'phosphochloridite. The phosphorylated DNA is synthesized off line by the usual methods, except that the 3'OH is protected as a silyl ether. The oligomer is then coupled to the activated chloridite on line, followed by oxidation, deprotection of the 3' silyl ether and continued homologation with sulfonyl nucleosides.

Chimeric Alternating DNA

A second type of oligomer is chimeric alternating sulfonyl/phosphoryl DNA. This chimeric type of DNA may be a useful antisense agent; and, it may be used to answer a structural question about the origin of the heteroduplex stability of neutral oligomers.

Alternating phosphoryl/sulfonyl DNA would be expected to be a useful antisense agent for several reasons. First, sulfonyl linkages at the 5' and 3' end of the oligo should engender stability against exonucleases, and second, internal sulfonyl groups may reduce the affinity of endonucleases for this hybrid oligomer. The oligo as a whole will have a smaller total charge than a normal DNA oligomer, and may therefore penetrate into cells more easily, but it will be structurally closer to a normal DNA oligomer than other sulfonyl-linked oligomers. Another use of this oligomer is its potential to answer a very interesting question about the affect of charge/charge interactions on heteroduplex stability. Examination of a double stranded DNA helix reveals that intrastrand phosphate residues are much closer to one another than the phosphate moieties on opposite strands. Because of this, it has been stated that it is intrastrand charge/charge repulsion that makes double helix formation salt dependent. Indeed, the stability of heteroduplexes between neutral and charged strands shows very little dependent on salt concentration. However, as appealing as the argument seems that it is intrastrand interactions that are important (because the charge/charge interactions depend on inverse distance and intrastrand phosphates are much closer together) this argument neglects one fact. The unmodified DNA or RNA strand still has a full complement of charged residues. Therefore, one would expect that the salt dependent on helix formation between neutral and charged oligomers would be reduced but still important. (Because the intrastrand phosphate residues on the charged strand still interact with one another.) In order to resolve this question, an alternating oligomer of neutral/charged linkages can be synthesized. Since this chimeric oligomer has no consecutive charged linkages, with respect to intrastrand interactions it should behave as a neutral oligomer. But with respect to interstrand interactions, it should behave as though it has about half the charge/charge interactions found in a normal DNA double helix. By studying the effect of salt concentration on the melting temperatures of these chimeric oligos, one may address whether it is intrastrand, or interstrand charge/charge interactions that are dominant.

A synthesis of the chimeric 5'-O-sulfonate and 3'-O-sulfonate alternating oligomers is shown in Scheme XVIII below.

often reported for the ability of modified homopolymers to form hetexoduplexes with DNA when A is substituted for T. $T_m$'s can be determined by monitoring absorption as a function of temperature. $T_m$ as a function of salt concentration can also be determined in order to study the affect of neutralizing one of the strands. It is also important to make sure that the melting profile is completely reversible, in order to be certain that thermodynamic effects are seen, rather than kinetic ones. Studies will be performed with both RNA and DNA. Since the in-vivo target of antisense agents is usually RNA it is important to be able to assess helix-forming capacity with RNA as well as DNA.

Triple helix formation can also be monitored by UV absorption as a function of temperature or the kinetics of triplex formation may be monitored by the restriction method developed in Dervan's group. Homothymidine oligomers are a suitable choice for these assays, although methylcytosine-containing oligos would also be suitable. It is hoped that the elimination of charge repulsion between the double helix and the neutral oligomers will lead to enhanced triple helix stability without the need for inclusion of devalent cations, or polyamines. The possibility that sulfonyl-

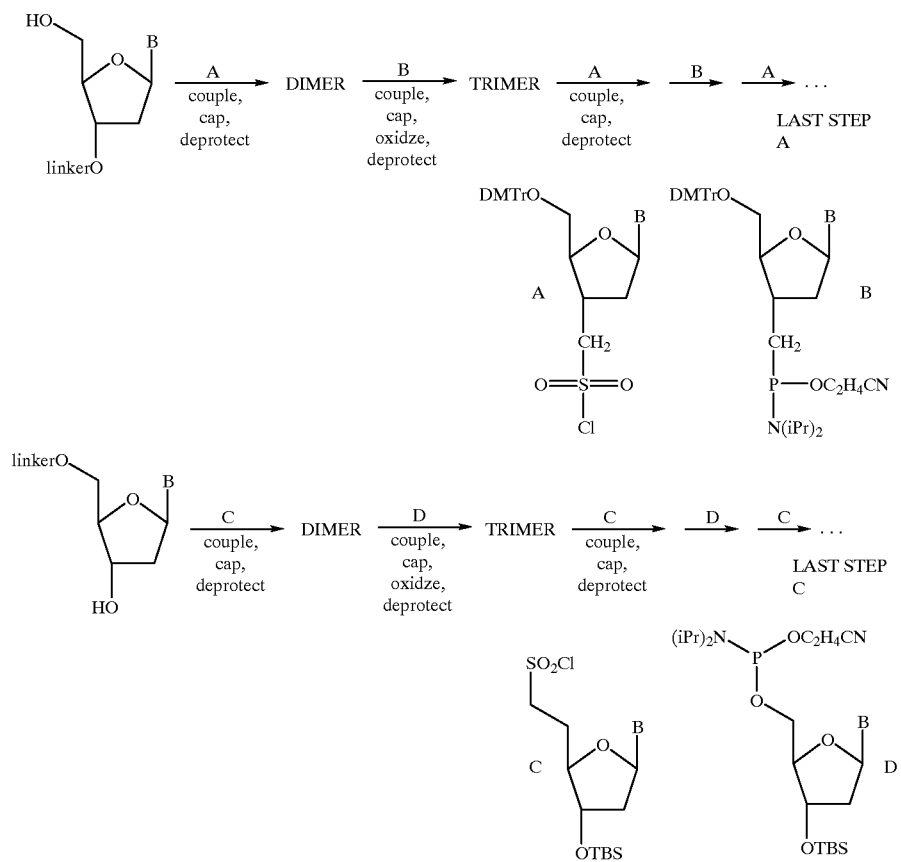

Scheme XVIII

Physical Studies

The helix forming capacities of the sulfonyl-linked oligomers described herein can be determined by measuring melting profiles. Homooctamers (or longer if necessary) of A and T (or U where appropriate) can be synthesized and then hybridized to complementary strands of RNA or DNA. It is probably necessary to study A and T homopolymers with modified linkages, given the substantial differences linked oligoribonulcleotides would form more stable triplexes than the DNA analogue because of structural considerations (an A-like form in the triple helix) can also be evaluated.

RNAse H Activity

The importance of RNAse activity is a central dogma in antisense strategies. One may evaluate the ability of the chimeric constructs described herein to serve as stimulators of RNAse H activity in the presence of complementary RNA.

RNAse H activity is also present in many viral reverse transcriptases, such as the HIV reverse transcriptase. These two RNAse H activities show different sequence specifities. The possibility of inhibiting the viral activity, while leaving the human activity unaffected can be probed by synthesizing RNA containing a single 5'-O-sulfonate linkage at the preferred cleavage site. This type of construct may inhibit the nuclease in one of two ways. It may simply function as a competitive inhibitor, or, it may actively alkylate the enzyme because of the electrophilicity of the 5'-O-sulfonate group. In either case, the fact that the viral enzyme shows different specificity than the human enzyme is a crucial factor in the design of such an agent as an antiviral.

DNA Polymerase Activity

The potential for using sulfonyl-linked DNA to address questions about protein-DNA interactions is quite significant. By using primers containing sulfonyl linkages at various sites, one can address questions about how an enzyme, such as DNA polymerase (Klenow for example) recognizes a primer strand. It is expected that the interaction between DNA polymerases and neutral oligomer would be minimal, however, a single sulfonyl linkage, or two in a row may not interfere with the ability of the primer to initiate synthesis, particularly if the linkage is downstream of the initial binding site. Short oligos (ca. 10–12 residues) containing a sulfonyl linkage at various positions can be tested as primers for DNA synthesis in the presence of a complementary template DNA strand. By using radiolabeled $\alpha^{-31}$ ATP as one of the triphosphates one should be able to quantitate oligonucleotide synthesis. If single linkages do not inhibit synthesis, consecutive linkages can be inserted. By determining the sensitivity of the polymerase to neutral areas of the template, one may gain a better understanding of the protein/DNA recognition element of binding and initiation of DNA synthesis. In addition, 5'-O-sulfonates may be used to function as affinity agents toward the polymerase. Several different possibilities exist: The primer may initiate DNA synthesis, but would alkylate the enzyme some of the time. One would expect to see time-dependent inactivitation of the polymerase under this scenario. Alternatively, the primer may stimulate binding (followed by alkylation), but not synthesis under any circumstances. This possibility can be checked in another way as well. By using a similar primer, but one which contains a 3'-O-sulfonate linkage, which is highly unlikely to alkylate the enzyme, one can test for binding and synthesis. Thus, the 51'-O-sulfonates and 3'-O-sulfonates are a very useful complementary combination for probing DNA/protein interactions.

For example, a sulfonate-linked thymidine dinucleoside was prepared as described. The 3' end of dinucleoside was attached to a controlled pore glass support via an oxalate ester linkage. The use of this linkage facilitated cleavage of the oligomer from the support at the end of the synthesis. In a control experiment, a sulfonate-linked dinucleoside was cleaved from the support in essentially quantitative yield using MeOH/$K_2CO_3$. Using standard phosphoramidite chemistry, the sulfonate-linked dimer was elongated to a twelve residue homooligomer of thymidine. This oligomer was then deblocked with diisopropylamine. After cleavage from the support (MeOH/$K_2CO_3$), the sulfonate-containing oligomer was purified by gel electrophoresis.

The thymidine homooligomer containing the 3' sulfonate linkage was incubated with a template strand (5'[C]$_{10}$ [A]$_{12}$3') in the presence of GTP, a DNA polymerase, and all appropriate cofactors. (Control experiments verified that, under these conditions, an analogous primer-template duplex formed with unmodified DNA was fully elongated by all three polymerases). The primer strand containing the 3' sulfonate linkage was elongated by all three enzymes, but most substantially by Klenow Fragment (KF) and T4 DNA polymerase (T4DP). Since the addition of each new residue moves the sulfonate linkage one position further from the 3' end of the primer, the formation of full length transcripts provides indirect evidence that the neutral linkage could also have been positioned at positions distal to the 3' end of the template without abolishing polymerase activity. However, unlike T4DP, KF shows a distinct (but not absolute) tendency to form a transcript in which only a single residue has been added. T7 DNA polymerase (T7DP) also reveals a less noticeable tendency to elongate the primer by a single residue. No other elongation intermediates were observed for any of the three enzymes tested. At low temperature, (ca. 0° C.) a temperature at which KF is known to be less processive, T7DP is virtually incapable of elongating the sulfonate-containing primer. In contrast to this finding, KF was capable of elongating the primer, but stopped after the addition of a single residue. T4DP was capable of forming full length transcripts, albeit slowly.

A sulfonate-linked dinucleoside containing a 3' phosphoramidite group was used to introduce the sulfonate linkage at positions further downstream from -1 of the primer strand. A complete set of oligomers containing single sulfonate linkages at -2 through -5 was prepared by this methodology. These primers were all substrates for the polymerization process. Only the modification at -2 (and -1 as previously mentioned) severely regarded activity, indicating that the enzyme probably normally has a tight association with a phosphodiester at these two positions. Sulfonamide-linked oligomers were also prepared in a manner analogous to those described for the sulfonate. The sulfonamide linkage supported more polymerization activity than the sulfonate, indicating that the sulfonamide is a better analogue of a phosphate than a sulfonate is. Oligomers containing a sulfonate or a sulfonamide linkage at the -1 position were completely stable toward the exonuclease activity of all the polymerases tested. While a normal oligomer of the same sequence was rapidly degraded. This demonstrates that the sulfonyl linkage is stable toward hydrolysis by exonucleases.

General Considerations: This application details the synthesis of monomer units which may then be used for coupling reactions to give sulfonyl-linked oligomers of various kinds. The applicant's methods are compatible with solid, or solution phase chemistry. Thus, it is not necessary to distinguish between monomers that are to be used for solution chemistry, or monomers to be used for solid phase chemistry.

This application does not distinguish explicitly between protected and unprotected nucleoside bases unless the specific subject of protection is being discussed. This is because it has been found that in virtually all cases, one may start with the appropriate protecting groups on the nucleoside, or they may be easily put in place. This application also details some novel approaches to the protection of the bases using TMS ethyl sulfonamides. This group has facilitated some of the applicant's syntheses and may, of course, be more broadly applied to DNA and RNA synthesis in general (in order to obviate the need for basic deblocking).

Although some of the applicant's analogues require lengthy syntheses and thus would not be favored for large scale production and use, they are nevertheless useful in the design of modified antisense agents. Thus, the present invention is useful for the design of effective antisense agents, for understanding structural requirements for double and triple helix formation, and for its provision of new chemistry to facilitate the synthesis of sulfonates having potential use as biologically active agents.

The present invention contemplates the improvement of antisense agents in two ways. First, agents are provided that will form the most stable possible double or triple helices, and these molecules are used for translation, processing, or transcription (triple helices) arrest. Second, advantage is taken of the activity of RNAse H to prepare oligos of high biochemical stability that contain recognition elements that will stimulate RNAse H activity.

Preparation of Sulfonyl Halides in General

In addition to its utility in preparing nucleoside sulfonates, the applicant's method is generally applicable to preparing sulfonyl chlorides with advantage. In particular, the reaction of the carbohydrate sulfonate (1) (Table 1) with a variety of reagents commonly used to synthesize sulfonyl chlorides give the desired acid chloride in modest yields at best (Table 1). Although there are a number of other methods for converting sulfonates into sulfonyl chlorides, there are few methods that would be compatible with the wide range of functionalities present in carbohydrates, nucleosides and phospholipids. In contrast, the applicant has discovered that halogenation with triphenylphosphine and a halogen donor (e.g. NCS, $Br_2$, $CCl_4$, $CVr_4$, etc.) is a reaction that is very tolerant of a wide range of functional groups such as those typically found in carbohydrates, nucleosides, and the acyl side of chains of phospholipids. Indeed, reaction of the sulfonate (1) with $PPh_3$ and an active halogenating agent gave the desired acid halide in good to excellent yields, depending on the halogen donor. For example, $PPh_3$/sulfuryl chloride in methylene chloride gives the sulfonyl chloride (2) in 87% isolated yield (Scheme XX). The method is tolerant of both acid sensitive (Table, entries 11 and 13) and base sensitive (Table 1, entries 16 and 17) functionalities and with the sole exception of 2-trimethylsilyl ethanesulfonyl chloride, which proved to be somewhat volatile (Table 1, entries 14 and 15), isolated yields of the sulfonyl chloride or the corresponding isopropyl ester were very good.

While the reagent combination of $PPh_3/SO_2Cl_2$ in methylene chloride is preferred for the conversion of sulfonate salts to sulfonyl chlorides, reasonable yields of the sulfonate esters may still be obtained when using other reagents such as NCS in combination with triphenylphospine (Table 1, entries 4–7). $PPh_3/CCl_4$ is a completely ineffective coupling agent under these particular conditions, as were DCC and DEAD (presumably, however, because of the absence of an acidic proton in the reaction medium). The use of $PPh_3$/$Br_2$ as an activating agent led to a good yield of the corresponding isopropyl sulfonate ester (5) upon quenching of the reaction with triethylamine/isopropanol (Table 1, entry 10).

The tetra-n-butyl ammonium sulfonates used for these reactions were prepared as described (Muskicki, B; Widlanski, T. S., *Tetrahedron Lett.*, 1991, Vol. 32, p 1267), or by titration of the corresponding acid with tetra-n-butyl ammonium hydroxide. The isopropyl sulfonate esters themselves were prepared by reaction of the corresponding iodides with a-lithio isopropyl methanesulfonate as previously described (Muskicki, B. Widlanski, T. S., *J. Org. Chem.*, 1990, Vol. 55, p. 4231), except for the galactose derivative (Table 1, entry 13). In this case, the corresponding iodide proved exceptionally unreactive, requiring the substitution of HMPA for DMPU in the reaction medium. Under these conditions, a 65% yield of the sulfonate ester was obtained upon reaction with the anion of isopropyl methanesulfonate (Scheme XIX).

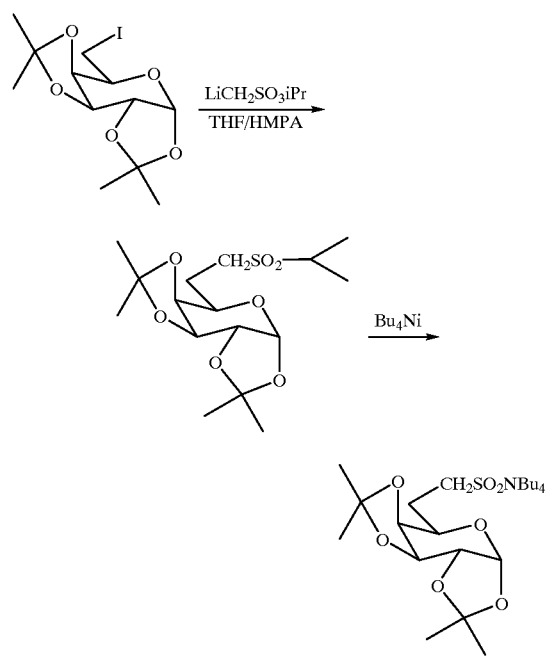

Scheme XIX

After deprotection with tetra-n-butyl ammonium iodide (61%), the salts could be purified by column chromatograpy on EtOH/EtOAc. The purified salts were then dissolved in Methylene chloride and filtered to remove residual silica. Although the use of tetra-n-butyl ammonium salts proved convenient, triethyl ammonium salts (prepared by titration of the corresponding acid, or by ion exchange chromatography) were also excellent substrates for conversion to sulfonyl chlorides using this reaction. In addition, the reaction need not be completely homogeneous, as evidenced by the reaction of the sodium salt of 2-trimethylsilyl ethane sulfonic acid (Table 1, entry 14), to give the known sulfonyl chloride. (See, Weinreb, S. M.; Demko, D. M.; Lessen, T. A., *Tetrahedron Lett.*, 1986, Vol. 27, p. 2099).

Although it is often convenient to convert the sulfonyl chloride directly to the isopropyl sulfonate ester (5) by treating the acid chloride with isopropanol/triethylamine in-site, it is straightforward to isolate the sulfonyl chloride when desired (see General Procedures below).

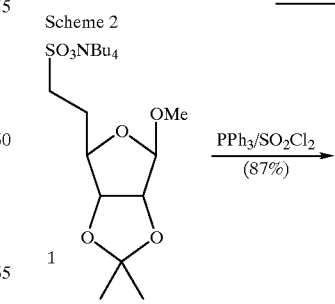

SCHEME XX

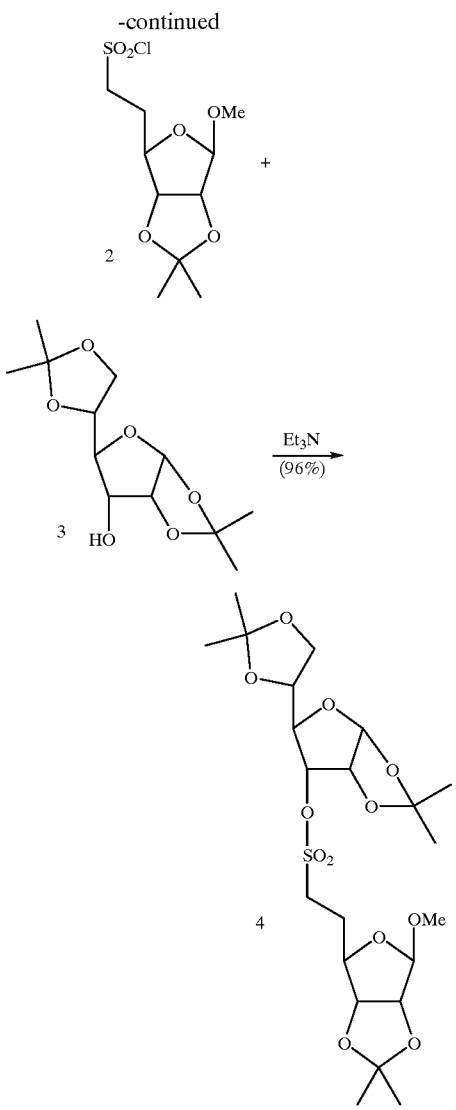

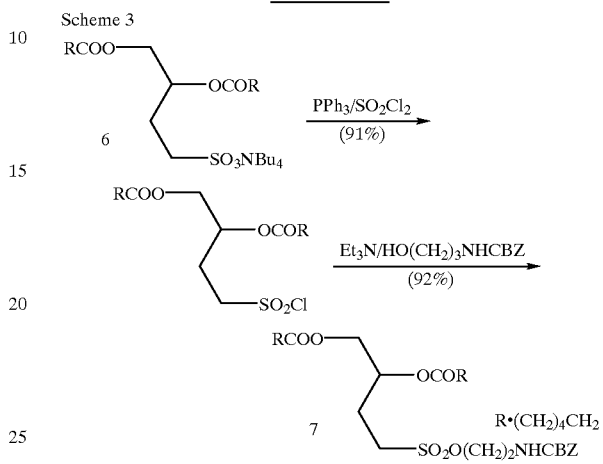

Coupling of the sulfonyl chloride (2), with secondary alcohols proved to be an excellent reaction. For example reaction of 2 with diacetone allose (3) gave the sulfonate ester (4) in 96% isolated yield (Scheme XX). This method is a substantial improvement over the previously reported coupling method. (See Muskicki, B. Widlanski, T. S., *J. Org. Chem.*, 1990, Vol. 55, p. 4231.) In addition, activation of the sulfonate analogue of phosphatidic acid (6) followed by coupling with CBZ protected ethanolamine gives the protected sulfonate analogue of phosphatidyl ethanolamine (7) (Scheme XXI). A similar coupling with O-benzyl CBZ-serine has also been effected. These phospholipid analogues may serve as useful affinity reagents for the labeling of proteins that process or metabolize phospholipids, or as inhibitors or phospholipases. In addition, these are uncharged phospholipid analogues that are isosteric to the parent phospholipids. It has long been thought that phospholipases will not recognize substrates or inhibitors that lack a negatively charged phosphoryl group. Recent results indicate that this notion is quite possibly incorrect. [Kuipers, O. P.; Dekker, N.; Verheji, H. M.; de Haas, G. H., *Biochemistry*, 1990, Vol. 29, p. 6094.] Such interactions have traditionally been probed by using phosphate triesters or methylphosphonates in order to mask the change of the phosphoryl group. Such analogues are not isosteric with the parent phosphate and have the added disadvantage of introducing a chiral center at phosphorus. These materials may prove useful in probing the specificity of phospholipid/protein interactions with respect to charge recognition. In addition, these materials may be used for the preparation of cationic liposomes that are structurally analogous to neutral liposomes prepared with phosphot-lipids.

The applicant also examined whether other acids can be converted to acid chlorides by this reagent. Reaction of $PPh_3/SO_2Cl_2$ with tetra-n-butyl ammonium diphenyl phosphate followed by quenching with ethanol in pyridine led to the phosphate triester in 63% isolated yield, indicating that this reaction may also be useful for the activation of phosphate diesters under very mild conditions. The same reaction does not appear to be preferred for the synthesis of acid chlorides from carboxylates. For example, treatment of triethylammonium benzoate with $PPh_3$/sulfuryl chloride, followed by the addition of ethanol in pyridine gave ethyl benzoate in only 16% yield. These results indicate that less nucleophilic salts such as sulfate monoesters, or sulfamates are likely to be better substrates for this type of activation than more nucleophilic ones.

General Procedures for Sulfonyl Halides

Sulfonyl Chlorides $PPh_3$ (0.170 g., 0.650 mmole) was dissolved in 0.8 ml $CH_2Cl_2$ at 0° C. $SO_2Cl_2$ (0.096 g, 0.714 mmole) was then added slowly. The ice bath was removed, and 1 (0.170 g, 0.325 mmole) in 1.7 ml $CH_2Cl_2$ was added dropwise over one minute. The reaction was monitored by TLC (EtOAc/ItOH 2:1) until the amount of 1 was reduced to minimum (usually 1 hr., insoluble salts require longer times). 70 ml of dry $Et_2$) in n-pentane (1:1) was then added to the reaction which was allowed to stand until the solution turned clear (30 min.). The supernatant was decanted into a dry flask, and the solvent was evaporated to dryness under reduced pressure. The residue was filtered through a plug of silica (hexane/EtOAc 3:1) and solvent evaporated to give pure sulfonyl chloride 2, which was immediately dried over $P_2O_5$ under high vacuum for several hours. Yield: 0.085 g (87%). $^1H$ NMR (CDCl$_3$, 300 MHz & 4.98 (s, 1H), 4.65 (d, 1H,J=6.64 Hz), 4.59 (d, 1H, J=5.86 Hz) 4.25 (dd, 1H, J-5.08 and 9.37 Hz), 3.79 (m, 2H), 3.38 (s, 3H), 2.27 (m, 2H), 1.47 (s, 3H), 1.31 (s, 3H). $^{13}C$ NMR (CDCl$_3$, 75.4 MHz) & 112.77, 110.15, 85.15, 84.11, 83.80, 62.54, 55.58, 29.99, 26.38, 24.90.

Isopropyl Sulfonate Esters

PPh$_3$ (0.157 g., 0.600 mmole) was dissolved in 1 ml CH$_2$Cl$_2$ at 0° C. SO$_2$Cl$_2$ (0.089 g, 0.659 mmole) was then added. After the ice bath was removed, and 1 (0.157 g, 0.300 mmole) in 1 ml CH$_2$Cl$_2$ was added. The reaction was then stirred for about one hour at rt and then quenched with an excess of isopropanol/triethylamine (5 ml. 1:1 by volume). After stirring for about one hour, the reaction was diluted with 9:1 Et$_2$ CH$_2$Cl$_2$ (70 ml). The solution was washed twice with 0.5 M phosphorus buffer (pH7) that had been saturated with MgSO$_4$ and then was dried over MgSO$_4$. Flash chromatography with hexane/EtOAc (7:4) gave 5 as a yellowish oil, 0.079 g (81%). This material was identical to that reported previously. (See, Muskicki, B. Widlanski, T. S., *J. Org. Chem.*, 1990, Vol. 55, p. 4231.)

Reaction of Sulfonyl Chlorides With Alcohols 2 (0.154 g, 0.512 mmole) and 3 (0.067 g, 0.256 mmole) were dissolved in CH$_2$Cl$_2$ (0.23 ml). To this solution was slowly added Et$_3$N (0.053 g, 0.512 mmole). After stirring for 10 min. at ambient temperature, the reaction was taken up in 9:1 Et$_2$/CH$_2$Cl$_2$ (100 ml) washed twice with 0.5 M phosphorus buffer (pH7) that had been saturated with MgSO$_4$ and then was dried over MgSO$_4$. Flash chromatography with hexane/EtOAc (7:6) as eluent gave 4 as a white solid, 0.128 g (96%), identical to previously reported material. (See, Muskicki, B, Widlanski, T. S. *J. Org. Chem.*, 1990, Vol. 55, p. 4231.)

Additional Exemplary Horner-Emmons and Glycosidation Chemistries

The addition of sulfonyl stabilized Horner-Emmons reagents to aldehydes also provides a useful method for coupling monosaccharides via a sulfonate linkage. For example, the 3-O mesylate of 1,2-5,6 diacetone allose (3) was converted to the Horner-Emmons reagent (4) by reaction with diethyl phosphorochloridate in the presence of KN[Si(Me)$_3$]$_2$. Reaction of the phosphonate 4 with the aldehyde (5), followed by reduction of the resulting α$^A$n-unsaturated sulfonate with NaBH$_4$ or [(Ph$_3$P)CuH]$_6$ (Mahoney, W. S.; Brestensky, D. M.; Stryker, J. M., *J. Am. Chem. Soc.*, 1988, Vol. 110, p. 291) (Scheme XXII) gave the disaccharide (6) in good yield. ([(PH$_3$P)CUH]$_6$ (Aldrich) was superior to NaBH$_4$ for reduction of these conjugated sulfonates.)

Scheme XXII

Eq. 2

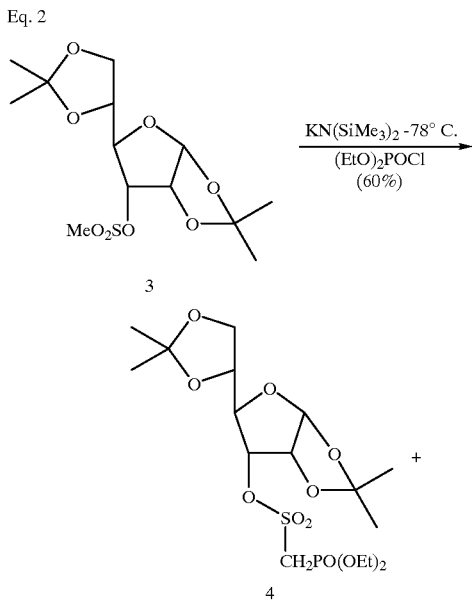

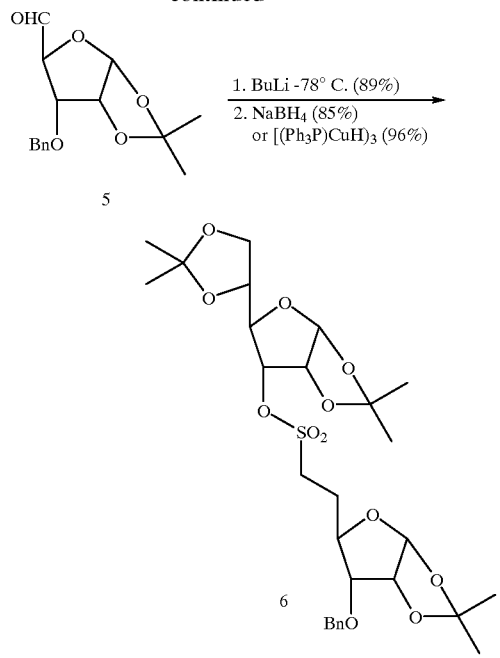

The applicant has also found that contrary to a published report stating the sulfonate-stabilized Horner-Emmons (7) reagents do not react well with ketones, (Carretero, J. C.: Demillequand, M.; Ghosez, L., *Tetrahedron*, 1987, Vol. 43, p. 5125) such reagents react readily with 1,2,5,6-diacetone ulose (8) to give a mixture of cis- and trans-a, B-unsaturated sulfonates (80% yield) which were reduced with NaBH$_4$ (85% yield) to give the saturated sulfonate (9) (Scheme XXIII). (The reaction of sulfonyl-stabilized phosphonate anions with carbohydrate ketones therefore provide simple access to non-hydrolyzable, isosteric and isoelectronic analogues of carbohydrates sulfated on secondary hydroxyl groups [e.g. heparin, Heparin sulfate, dermatan sulfate chondroitin sulfate, keratan sulfate and many others (for a recent review summarizing a variety of sulfated carbohydrates see, Kresse, H; Glossl, *J. Advances in Enzymology and Related Areas of Molecular Biology*, 1990, Vol. 60, p. 217)]. To applicant's knowledge, this is the first simple synthesis of such compounds.) Synthesis of the corresponding sulfone units (10) was accomplished in an analogous fashion, by using the sulfone-stabilized Horner-Emmons reagents (11) (Shahak, I; Almog, *J. Synthesis*, 1969, Vol. 170) instead of sulfonate-stabilized anion (56% yield), and adding N,N-dimethylproplyeneurea to the reaction mixture. The resulting a,B-unsaturated sulfone was reduced with [(Ph$_3$P)CuH]$_6$ to give the saturated sulfone 10 in 88% yield (Scheme XXIII).

Scheme XXIII

Eq. 3

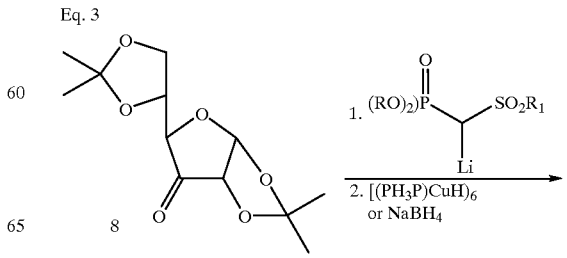

-continued

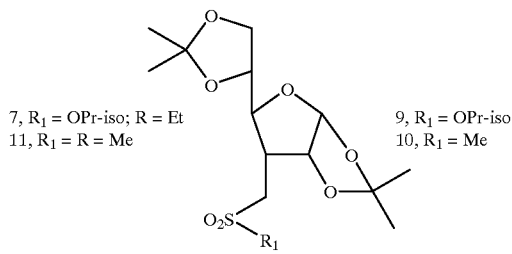

7, $R_1$ = OPr-iso; R = Et
11, $R_1$ = R = Me

9, $R_1$ = OPr-iso
10, $R_1$ = Me

All publications cited herein are indicative of the level of ordinary skill in the pertinant art and are hereby incorporated herein by reference as is fully set forth.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What is claimed is:

1. An oligonucleotide having at least one repeating unit having the formula:

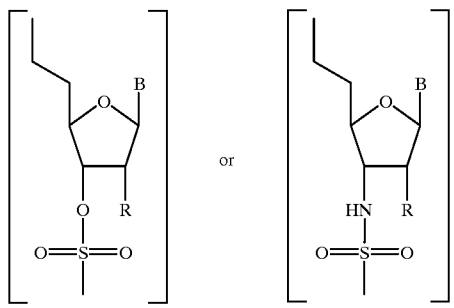

wherein R=—H or a protected or unprotected hydroxyl group, and B is a protected or unprotected purine or pyrimidine base selected from the group consisting of cytidine, adenine and guanine.

2. An oligonucleotide having at least one repeating unit having the formula:

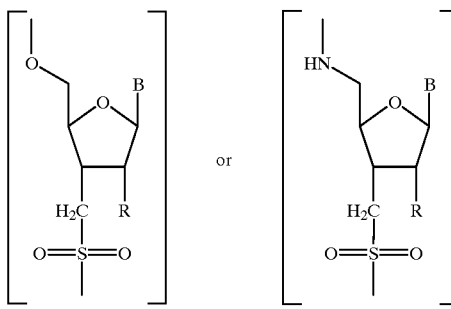

wherein R=—H or a protected or unprotected hydroxyl group, and B is a protected or unprotected purine or pyrimidine base.

3. The oligonucleotide of claim 1, having the formula

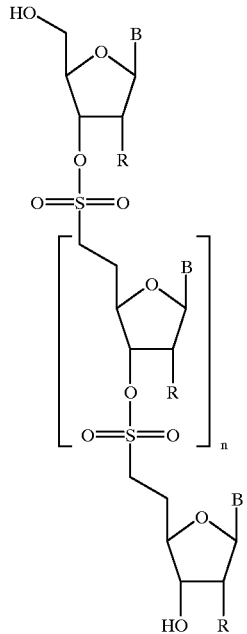

wherein R and B are as previously defined, and n is an integer from 1 to about 200.

4. The oligonucleotide of claim 2, having the formula

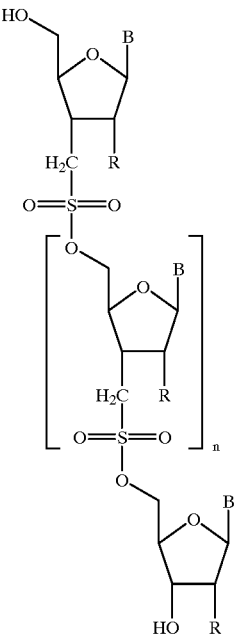

wherein R and B are as previously defined, and n is an integer from 1 to about 200.

5. The oligonucleotide of claim 1, having the formula

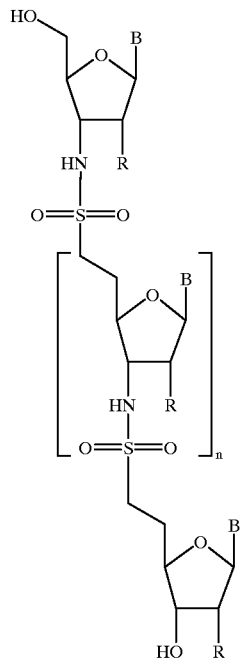

wherein R and B are as previously defined, and N is an integer from 1 to about 200.

6. The oligonucleotide of claim 2, having the formula

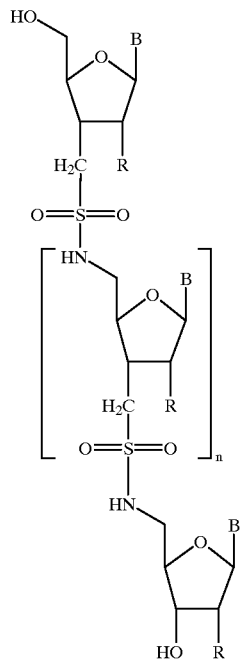

wherein R and B are as previously defined, and n is an integer from 1 to about 200.

7. A nucleoside monomer of the formula

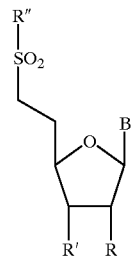

wherein:
R=—H or a protected or unprotected hydroxyl group;
R'=a protected or unprotected hydroxyl or amino group;
R"=Cl, Br or a group of the formula —O—R'" wherein R'" is a $C_1$ to $C_{10}$ alkyl group; and
B=a protected or unprotected purine or pyrimidine base selected from the group consisting of thymine, cytidine, adenine and guanine, with the proviso that when B is thymine R is a protected or unprotected hydroxyl group and/or R' is a protected or unprotected amino group.

8. The nucleoside monomer of claim 7, wherein R=—H.

9. The nucleoside monomer of claim 7, wherein R=protected or unprotected hydroxyl.

10. The nucleoside monomer of claim 7, wherein R" is Cl or Br.

11. The nucleoside monomer of claim 7, wherein R' is a group of the formula —O—R'" wherein R'" is $C_1$ to $C_{10}$ alkyl.

12. The nucleoside monomer of claim 7 wherein B is protected or unprotected thymine.

13. The nucleoside monomer of claim 7, wherein B is protected or unprotected adenine.

14. The nucleoside monomer of claim 7, wherein B is protected or unprotected guanine.

15. The nucleoside monomer of claim 7, wherein B is protected or unprotected cytidine.

16. A nucleoside monomer of the formula

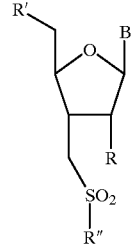

wherein:
R=—H or a protected or unprotected hydroxyl group;
R'=a protected or unprotected hydroxyl or amino group;
R"=Cl, Br or a group of the formula —O—R'" wherein R'" is a $C_1$ to $C_{10}$ alkyl group; and
B=a protected or unprotected purine or pyrimidine base.

* * * * *